United States Patent
Joe et al.

(10) Patent No.: US 10,358,142 B2
(45) Date of Patent: Jul. 23, 2019

(54) SAFE DRIVING SUPPORT VIA AUTOMOTIVE HUB

(71) Applicant: QUALCOMM Incorporated, San Diego, CA (US)

(72) Inventors: Gregory Hobert Joe, San Jose, CA (US); Arthur James, San Jose, CA (US); Srdjan Miocinovic, Los Gatos, CA (US); Sandipan Kundu, Santa Clara, CA (US)

(73) Assignee: QUALCOMM Incorporated, San Diego, CA (US)

( * ) Notice: Subject to any disclaimer, the term of this patent is extended or adjusted under 35 U.S.C. 154(b) by 181 days.

(21) Appl. No.: 15/461,468

(22) Filed: Mar. 16, 2017

(65) Prior Publication Data
US 2018/0265095 A1    Sep. 20, 2018

(51) Int. Cl.
*B60W 40/08* (2012.01)
*B60W 50/00* (2006.01)
(Continued)

(52) U.S. Cl.
CPC ......... *B60W 50/0098* (2013.01); *A61B 5/021* (2013.01); *A61B 5/024* (2013.01);
(Continued)

(58) Field of Classification Search
CPC ............. B60W 50/0098; B60W 40/08; B60W 2040/0881; B60W 2040/0872;
(Continued)

(56) References Cited

U.S. PATENT DOCUMENTS

| 8,738,523 B1 | 5/2014 | Sanchez et al. |
| 9,613,515 B2 * | 4/2017 | Prakah-Asante ............ G08B 21/0453 |

(Continued)

FOREIGN PATENT DOCUMENTS

| DE | 102008042342 A1 | 4/2010 |
| EP | 3109114 A1 | 12/2016 |

(Continued)

OTHER PUBLICATIONS

International Search Report and Written Opinion—PCT/US2018/015395—ISA/EPO—Apr. 19, 2018.

*Primary Examiner* — Nadeem Odeh
(74) *Attorney, Agent, or Firm* — Muncy, Geissler, Olds & Lowe, P.C./Qualcomm

(57) ABSTRACT

A method for providing safe-driving support of a vehicle includes obtaining occupant data and vehicle data received at a vehicle hub. The occupant data is related to an identity and health status of an occupant and the vehicle data is related to a status of the vehicle. The method also includes obtaining action data based on an application of the occupant data and vehicle data to a machine learning safe-driving model. The machine learning safe-driving model is associated with a user profile of the occupant that is identified from among a plurality of user profiles based on the occupant data. A server maintains a plurality of user profiles, each having a respective machine learning safe-driving model. The action data relates to an action to be performed by the vehicle while the occupant is located in the vehicle.

24 Claims, 16 Drawing Sheets

(51) Int. Cl.
| | |
|---|---|
| *B60W 10/04* | (2006.01) |
| *B60W 10/30* | (2006.01) |
| *B60W 50/14* | (2012.01) |
| *A61B 5/18* | (2006.01) |
| *A61B 5/00* | (2006.01) |
| *A61B 5/021* | (2006.01) |
| *A61B 5/024* | (2006.01) |
| *B60K 28/02* | (2006.01) |
| *B60K 28/06* | (2006.01) |
| *B60W 40/04* | (2006.01) |
| *B60W 40/06* | (2012.01) |
| *B60W 40/09* | (2012.01) |
| *G06N 20/00* | (2019.01) |
| *G01S 19/13* | (2010.01) |
| *H04L 29/08* | (2006.01) |

(52) U.S. Cl.
CPC .............. *A61B 5/18* (2013.01); *A61B 5/4845* (2013.01); *B60K 28/02* (2013.01); *B60K 28/06* (2013.01); *B60W 10/04* (2013.01); *B60W 10/30* (2013.01); *B60W 40/04* (2013.01); *B60W 40/06* (2013.01); *B60W 40/08* (2013.01); *B60W 40/09* (2013.01); *B60W 50/14* (2013.01); *G06N 20/00* (2019.01); *B60W 2040/089* (2013.01); *B60W 2040/0809* (2013.01); *B60W 2040/0818* (2013.01); *B60W 2040/0872* (2013.01); *B60W 2040/0881* (2013.01); *B60W 2420/42* (2013.01); *B60W 2540/22* (2013.01); *B60W 2540/24* (2013.01); *B60W 2540/26* (2013.01); *B60W 2540/28* (2013.01); *B60W 2540/30* (2013.01); *B60W 2550/12* (2013.01); *B60W 2550/40* (2013.01); *B60W 2550/408* (2013.01); *B60W 2710/06* (2013.01); *B60W 2710/30* (2013.01); *B60W 2720/10* (2013.01); *G01S 19/13* (2013.01); *H04L 67/12* (2013.01)

(58) Field of Classification Search
CPC ......... B60W 2540/22; B60W 2540/24; B60W 2540/26; B60K 28/02; B60K 28/06
USPC ....................................................... 701/36, 70
See application file for complete search history.

(56) References Cited

U.S. PATENT DOCUMENTS

| | | |
|---|---|---|
| 2008/0258890 A1 | 10/2008 | Follmer et al. |
| 2013/0073122 A1 | 3/2013 | Hoshiya |
| 2015/0025917 A1 | 1/2015 | Stempora |
| 2015/0246673 A1* | 9/2015 | Tseng ................... B60W 30/00 701/23 |
| 2016/0264131 A1* | 9/2016 | Chan ................... B60W 30/025 |
| 2017/0355377 A1* | 12/2017 | Vijaya Kumar ...... B60W 40/08 |
| 2017/0370732 A1* | 12/2017 | Bender ................ G05D 1/0088 |

FOREIGN PATENT DOCUMENTS

| | | |
|---|---|---|
| KR | 20140129710 A | 11/2014 |
| WO | 2018031759 A2 | 2/2018 |

* cited by examiner

SAFE DRIVING SUPPORT VIA AUTOMOTIVE HUB

FIELD OF DISCLOSURE

This disclosure relates generally to providing safe-driving support, and in particular, but not exclusively, relates to the providing safe-driving support via an automotive hub.

BACKGROUND

Improving the safe driving of vehicles is a continued desire, in part, due the increased of the number of vehicles on the road. Despite this desire, the number of vehicle fatalities remains high, due, in part, to one or more unsafe driving practices (e.g., alcohol impaired drivers, young inexperienced drivers, distracted drivers, and drowsy drivers, etc.).

Some existing technical solutions that attempt to improve driving safety are typically narrow in scope of the specific problem being addressed and often require vehicle modification by the mounting of an aftermarket sensor. For example, a breathalyzer may be mounted to the vehicle to prevent the starting of the vehicle's engine unless a measured blood/alcohol level is below a certain limit. Similarly, a sensor may be mounted to the vehicle to detect cell phone usage, where an application installed on the phone may disable certain functions (e.g., texting) of the phone while the vehicle is in motion.

However, these solutions often depend on driver cooperation to work, require vehicle modification, lack robustness to detect a variety of unsafe driving practices, and are limited in the sensor data available to make such decisions.

SUMMARY

The following presents a simplified summary relating to one or more aspects and/or examples associated with the mechanisms disclosed herein for providing safe-driving support of a vehicle. As such, the following summary should not be considered an extensive overview relating to all contemplated aspects and/or examples, nor should the following summary be regarded to identify key or critical elements relating to all contemplated aspects and/or examples or to delineate the scope associated with any particular aspect and/or example. Accordingly, the following summary presents certain concepts relating to one or more aspects and/or examples relating to the mechanisms disclosed herein for providing safe-driving support in a simplified form to precede the detailed description presented below.

According to one aspect, a method for providing safe-driving support of a vehicle includes obtaining occupant data and vehicle data received at a vehicle hub. The occupant data is related to an identity and health status of an occupant and the vehicle data is related to a status of the vehicle. The method also includes obtaining action data based on an application of the occupant data and vehicle data to a machine learning safe-driving model. The machine learning safe-driving model is associated with a user profile of the occupant that is identified from among a plurality of user profiles based on the occupant data. A server maintains a plurality of user profiles, each having a respective machine learning safe-driving model. The action data relates to an action to be performed by the vehicle while the occupant is located in the vehicle.

According to another aspect, a vehicle hub for providing safe-driving support of a vehicle includes a processor and a memory coupled to the processor. The processor and memory are configured to direct the vehicle hub to receive occupant data and vehicle data at the vehicle hub. The occupant data is related to an identity and health status of an occupant of the vehicle and the vehicle data is related to a status of the vehicle. The processor and memory are further configured to obtain action data based on an application of the occupant data and vehicle data to a machine learning safe-driving model associated with a user profile of the occupant. The user profile is identified from among a plurality of user profiles based on the occupant data and the machine learning safe-driving model is one of a plurality of machine learning safe-driving models. Each of the plurality of machine learning safe-driving models are associated with a respective one of the plurality of user profiles maintained at a server. The action data relates to an action to be performed by the vehicle while the occupant is located in the vehicle. The processor and memory are further configured to direct the vehicle hub to perform the action at the vehicle in response to the action data.

According to another aspect, a server for providing safe-driving support of a vehicle includes a processor and a memory coupled to the processor. The processor and memory are configured to direct the server to obtain occupant data and vehicle data received at a vehicle hub of the vehicle. The occupant data is related to an identity and health status of an occupant of the vehicle and the vehicle data is related to a status of the vehicle. The processor and memory are further configured to direct the server to identify a user profile of the occupant from among a plurality of user profiles based on the occupant data and to apply the occupant data and vehicle data to a machine learning safe-driving model to obtain action data. The machine learning safe-driving model is associated with the user profile of the occupant and the machine learning safe-driving model is one of a plurality of machine learning safe-driving models. Each of the plurality of machine learning safe-driving models is associated with a respective one of the plurality of user profiles maintained at the server. The action data relates to an action to be performed by the vehicle while the occupant is located in the vehicle. The processor and memory are further configured to direct the server to wirelessly transmit the action data to the vehicle hub to perform the action at the vehicle.

According to yet another aspect, apparatus for providing safe-driving support of a vehicle includes (1) means for obtaining occupant data and vehicle data received at a vehicle hub of the vehicle, and (2) means for obtaining action data based on an application of the occupant data and vehicle data to a machine learning safe-driving model associated with a user profile of the occupant. The occupant data is related to an identity and health status of an occupant of the vehicle and the vehicle data is related to a status of the vehicle. The user profile is identified from among a plurality of user profiles based on the occupant data and the machine learning safe-driving model is one of a plurality of machine learning safe-driving models, where each of the plurality of machine learning safe-driving models is associated with a respective one of the plurality of user profiles maintained at a server. Furthermore, the action data relates to an action to be performed by the vehicle while the occupant is located in the vehicle.

According to another aspect, a non-transitory computer-readable storage medium includes program code stored thereon for providing safe-driving support of a vehicle. The program code includes instructions to: (1) obtain occupant data and vehicle data received at a vehicle hub of the vehicle, and (2) obtain action data based on an application of the occupant data and vehicle data to a machine learning safe-driving model associated with a user profile of the occupant. The occupant data is related to an identity and health status of an occupant of the vehicle and the vehicle data is related to a status of the vehicle. The user profile is identified from among a plurality of user profiles based on the occupant data and the machine learning safe-driving model is one of a plurality of machine learning safe-driving models, where each of the plurality of machine learning safe-driving models is associated with a respective one of the plurality of user profiles maintained at a server. Furthermore, the action data relates to an action to be performed by the vehicle while the occupant is located in the vehicle.

Other objects and advantages associated with the mechanisms disclosed herein for providing safe-driving support described herein will be apparent to those skilled in the art based on the accompanying drawings and detailed description.

BRIEF DESCRIPTION OF THE DRAWINGS

A more complete appreciation of aspects of the present disclosure and many of the attendant advantages thereof will be readily obtained as the same becomes better understood by reference to the following detailed description when considered in connection with the accompanying drawings which are presented solely for illustration and not limitation of the aspects provided herein, and in which.

DETAILED DESCRIPTION

Various aspects are disclosed in the following description and related drawings. Alternate aspects may be devised without departing from the scope of the disclosure. Additionally, well-known elements of the disclosure will not be described in detail or will be omitted so as not to obscure the relevant details of the disclosure.

The words "exemplary" and/or "example" are used herein to mean "serving as an example, instance, or illustration." Any aspect described herein as "exemplary" and/or "example" is not necessarily to be construed as preferred or advantageous over other aspects. Likewise, the term "aspects of the disclosure" does not require that all aspects of the disclosure include the discussed feature, advantage or mode of operation.

The terminology used herein is for the purpose of describing particular example only and not to limit any example disclosed herein. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

Further, many examples are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer readable storage medium having stored therein a corresponding set of computer instructions that upon execution would cause an associated processor to perform the functionality described herein. Thus, the various aspects of the present disclosure may be embodied in a number of different forms, all of which have been contemplated to be within the scope of the claimed subject matter. In addition, for each of the example described herein, the corresponding form of any such example may be described herein as, for example, "logic configured to" perform the described action.

Figure 1:
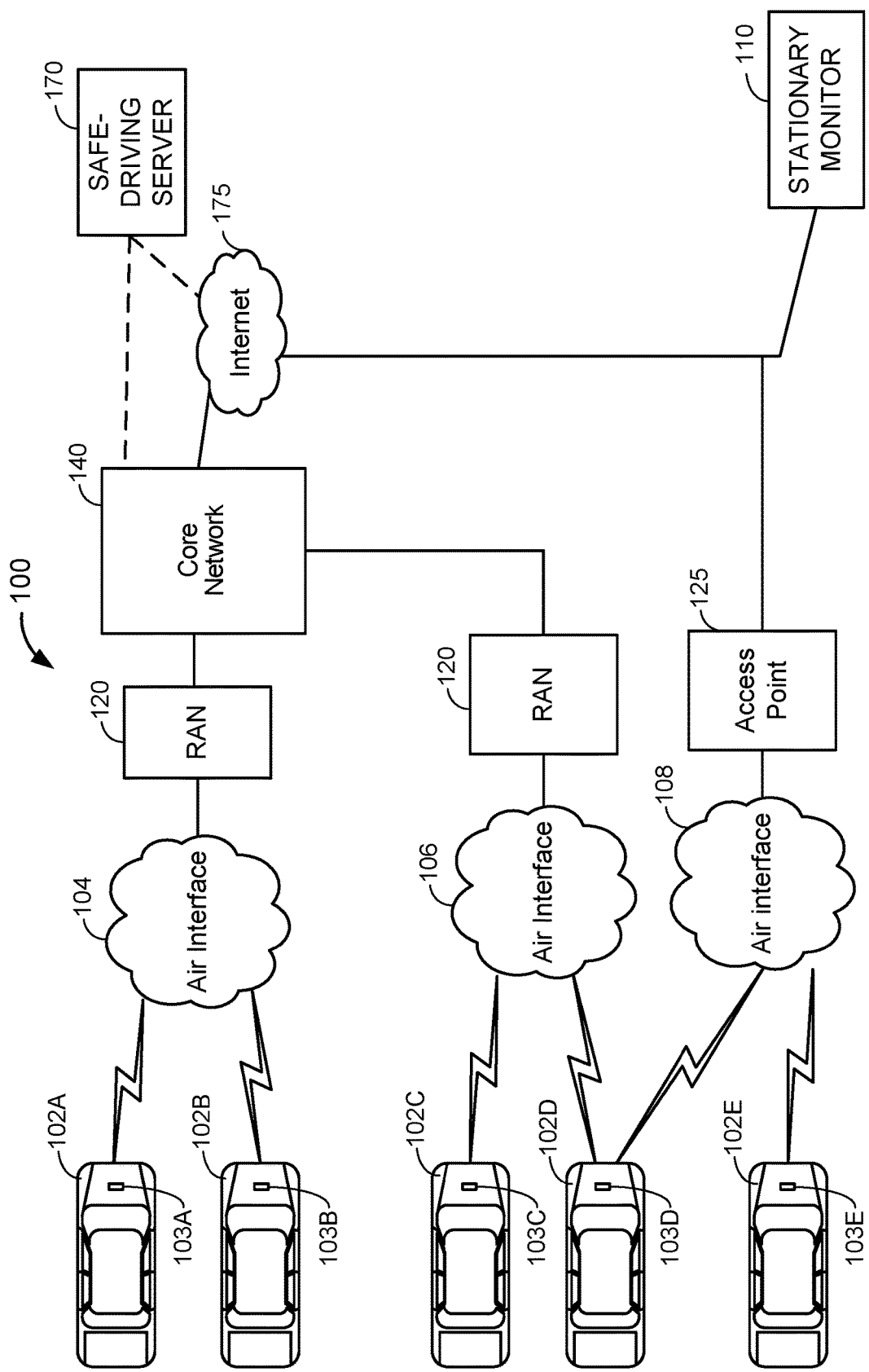
FIG. 1 illustrates an example operating environment for several vehicles and a server that can provide safe-driving support, according to aspects of the disclosure.

FIG. 1 illustrates an example operating environment 100 for several vehicles 102A-102E that each include a vehicle hub 103A-103E for providing safe-driving support of a respective vehicle, according to aspects of the disclosure.

Each vehicle hub of vehicles 102A-102E are configured to communicate with an access network (e.g., a radio access network (RAN) 120 or an access point 125, etc.) over a physical communications interface or layer, shown in FIG. 1 as air interfaces 104, 106, 108. The air interfaces 104 and 106 can comply with a given cellular communications protocol (e.g., CDMA, EVDO, eHRPD, GSM, EDGE, W-CDMA, LTE, etc.), while the air interface 108 can comply with a wireless IP protocol (e.g., IEEE 802.11). The RAN 120 includes a plurality of access points that serve vehicles 102A-102D over air interfaces, such as the air interfaces 104 and 106. The access points in the RAN 120 can be referred to as access nodes or ANs, access points or APs, base stations or BSs, Node Bs, eNode Bs, and so on. These access points can be terrestrial access points (or ground stations), or satellite access points. The RAN 120 is configured to connect to a core network 140 that can perform a variety of functions, including mediating an exchange of packet-switched (PS) data with external networks such as Internet 175. The Internet 175 includes a number of routing agents and processing agents (not shown in FIG. 1). In FIG. 1, a stationary monitor 110 is shown as connecting to the Internet 175 directly (i.e., separate from the core network 140, such as over an Ethernet connection of WiFi or 802.11-based network).

Also shown in FIG. 1 is an access point 125 that is separate from the RAN 120. The access point 125 may be connected to the Internet 175 independent of the core network 140 (e.g., via an optical communication system such as FiOS, a cable modem, etc.). The air interface 108 may serve vehicle 102D and 102E over a local wireless connection, such as IEEE 802.11 in an example. The stationary monitor 110 is shown with a wired connection to the Internet 175, such as a direct connection to a modem or router, which can correspond to the access point 125, itself, in an example (e.g., for a WiFi router with both wired and wireless connectivity).

Many vehicles include a number of in-vehicle sensors and/or communication interfaces. However, these sensors and communication interfaces are often independent, disparate, and not-co-located with respect to each other. Thus, culmination of data from multiple sources is often difficult, if not impossible. Accordingly, aspects of the present disclosure include the use of a vehicle hub that is incorporated into the vehicle itself. The vehicle hub functions as a center for in-vehicle sensors, context data collection, data fusion, and data processing. The vehicle hub also provides a wireless interface to the cloud (e.g., a safe-driving server 170) for processing of the data collected.

As will be described in further detail below, each vehicle hub 103A-103E may receive data from multiple in-vehicle sensors and/or systems. For example, the vehicle hub may receive data related to the vehicle chassis, vehicle interior state (e.g., image captures, doors open/closed, seat position, etc.), vehicle diagnostics (e.g., speed, engine information, gas levels, etc.), infotainment (e.g., navigation usage, multimedia services utilized, phone pairings, etc.), dashboard status, and/or powertrain status. In addition, the vehicle hub may also be connected to one or more communication interfaces that allow the vehicle hub to receive and/or communicate with one or more devices that are separate from the vehicle, itself. For example, FIG. 1 illustrates the vehicle hub 103A of vehicle 102A in wireless communication with vehicle hub 103B of vehicle 102B. Vehicle hub 103A may also be in wireless communication with a mobile device (e.g., smart phone, tablet, wearable device, etc.) located within vehicle 102A, a stationary monitor 110 (e.g., road side unit, toll collector, etc.), as well as a server, such as safe-driving server 170.

Some aspects of the present disclosure include the leveraging of data collected at the vehicle hub for promoting a safe-driving experience. In one example, the data collected at the vehicle hub is wirelessly transmitted to a server (e.g., safe-driving server 170), where the server applies the data to a machine-learning safe-driving model. The machine-learning safe-driving model may represent a model of driving and/or occupant activity upon which action data may be generated. For example, the machine-learning safe-driving model may include performing an analysis technique such as a machine learning technique or other advanced technique for data analysis. The machine learning technique may be a supervised, unsupervised, or a reinforcement learning technique. Examples of supervised learning techniques include K-nearest neighbor (KNN), Naive Bayes, logistic regression, support vector machine (SVM), and others. Other supervised learning analysis techniques include linear or polynomial regression analysis, decision tress analysis, and random forests analysis. Examples of unsupervised learning analysis techniques include association analysis, clustering analysis, dimensionality reduction analysis, hidden Markov model analysis techniques, and others. Examples of clustering analysis techniques include K-means, principal component analysis (PCA), singular value decomposition (SVD), incremental clustering, and probability-based clustering techniques. The reinforcement learning technique may be, for example, a Q-learning analysis technique. The techniques described above are some examples of machine learning techniques that may be utilized by the machine learning safe driving model to generate action data. These are not intended to be limiting.

The action data that is generated by the machine learning safe driving model relates to an action that is to be performed by the vehicle in order to improve the safe-driving of the vehicle. The vehicle then implements an action based on the action data. By way of example, the action may include implementing parental controls, limiting/disabling cell data, disabling text messaging, limiting multimedia content, deactivating the engine, notifying another person (family member or taxi cab), limiting a maximum speed of vehicle, monitoring the health of occupant, planning routing of the navigation system (minimize traffic/avoid highways), and/or providing safe driving recommendations (e.g., alert driver to slow down, or of upcoming road obstruction, etc.).

As will be described in more detail below, the safe-driving server 170 is configured to provide safe-driving support based on occupant data and vehicle data received from a respective vehicle hub 103A-103E of a vehicle 102A-102E and/or data received from stationary monitor 110. The safe-driving server 170 can be implemented as a plurality of structurally separate servers, or alternately may correspond to a single server.

As used herein, the term "vehicle" may refer to any type of mobile machine which may transfer information over a network and also have vehicle-hub functionality. The vehicle may be any motor vehicle (motorcycle, car, truck, bus), railed vehicle (train, tram, light-rail), or watercraft (ship, boat), whether manned or unmanned.

Figure 2A:
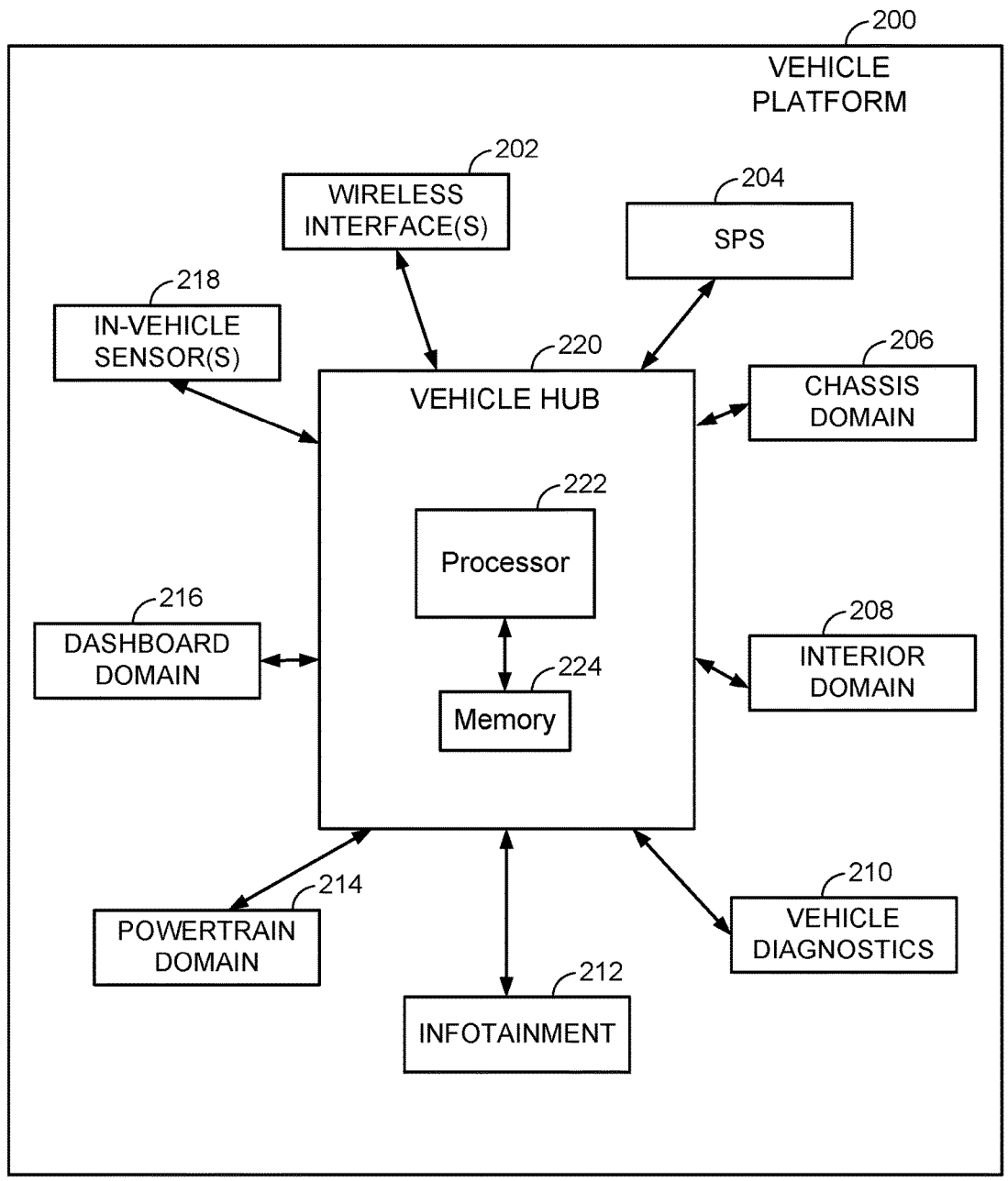
FIG. 2A illustrates an example vehicle platform including a vehicle hub for providing safe-driving support, according to aspects of the disclosure.

FIG. 2A illustrates an example vehicle platform 200 including a vehicle hub 220 for providing safe-driving support, according to aspects of the disclosure. The various features and functions illustrated in the diagram of FIG. 2A may be connected together using a common bus which is meant to represent that these various features and functions are operatively coupled together. Those skilled in the art will recognize that other connections, mechanisms, features, functions, or the like, may be provided and adapted as necessary to operatively couple and configure an actual vehicle hub 220. Further, it is also recognized that one or more of the features or functions illustrated in the example of FIG. 2A may be further subdivided or two or more of the features or functions illustrated in FIG. 2A may be combined. The illustrated vehicle platform 200 of FIG. 2A is one possible implementation of a platform incorporated into one or more of the vehicles 102A-102E of FIG. 1.

As shown in FIG. 2A, vehicle hub 220 is coupled to a wireless interface 202, a satellite positioning system (SPS) 204, a chassis domain 206, and interior domain 208, a vehicle diagnostics system 210, an infotainment system 212, a powertrain domain 214, a dashboard domain 216, and one or more in-vehicle sensors 218. However, vehicle hub 220 may be additionally coupled to various other several sensors, systems, interfaces, domains of the vehicle platform 200, not explicitly illustrated in FIG. 2A. In operation, vehicle hub 220 is configured to receive data from the wireless interface 202, the satellite positioning system (SPS) 204, the chassis domain 206, and the interior domain 208, the vehicle diagnostics system 210, the infotainment system 212, the powertrain domain 214, the dashboard domain 216, and one or more of the in-vehicle sensors 218. In one aspect, the data may be received at the vehicle hub 220 periodically, or on demand (e.g., in response to a request generated by the vehicle hub 220). The data received at the vehicle hub may include occupant data and vehicle data. In one aspect, the occupant data refers to data that is related to an identity of an occupant of the vehicle, including a driver of the vehicle and/or a passenger of the vehicle. The vehicle data refers to data that is related to a status of the vehicle, such as location, speed, diagnostics, etc.

The wireless interface 202 may include a wide area network (WAN) transceiver that may be connected to one or more antennas. The WAN transceiver may comprise any suitable devices, hardware, and/or software for communicating with and/or detecting signals to/from RAN 120, and/or directly with other wireless devices within a network. In one aspect, the WAN transceiver may comprise a CDMA communication system suitable for communicating with a CDMA network of wireless base stations; however in other aspects, the wireless communication system may comprise another type of cellular telephony network, such as, for example, TDMA or GSM. Additionally, any other type of wide area wireless networking technologies may be used, for example, WiMAX (IEEE 802.16), etc. The wireless interface 202 may also include one or more local area network (LAN) transceivers that may be connected to one or more antennas. The LAN transceiver may comprise any suitable devices, hardware, and/or software for communicating with and/or detecting signals to/from Access point 125, and/or directly with other wireless devices within a network. In one aspect, the LAN transceiver may comprise a Wi-Fi (802.11x) communication system suitable for communicating with one or more wireless access points; however in other aspects, the LAN transceiver may comprise another type of local area network, personal area network, (e.g., Bluetooth). Additionally, any other type of wireless networking technologies may be used, for example, Ultra Wide Band, ZigBee, wireless USB etc.

In some aspects, vehicle platform 200 can exploit signals from RANs, from APs, or any combination of the two. The specific type of AP being utilized by the vehicle platform 200 may depend upon the environment of operation. Moreover, the vehicle platform 200 may dynamically select between the various types of RANs/APs in order to achieve an optimal connection to safe-driving server 170 (see FIG. 1). In other examples, various network elements may operate in a peer-to-peer manner, whereby, for example, the vehicle platform 200 may be replaced with the WAP, or vice versa. Other peer-to-peer implementations may include another vehicle platform (not shown) acting in place of one or more WAP.

The SPS receiver 204 may be connected to the one or more antennas for receiving satellite signals. The SPS receiver 204 may comprise any suitable hardware and/or software for receiving and processing SPS signals. The SPS receiver 204 requests information and operations as appropriate from the other systems, and performs the calculations necessary to determine the vehicle platform's 200 position using measurements obtained by any suitable SPS algorithm.

The chassis domain 206 may include one or more sensors configured to generate data related to speed, pressure, position, temperature, status, and/or performance of one or more chassis-related functions of the vehicle such as the braking system, the vehicle wheels, suspension, etc.

The interior domain 208 may include one or more sensors configured to generate data related to the status of the interior of the vehicle (e.g., image captures, doors open/closed, seat position, etc.).

The vehicle diagnostics system 210 may include one or more sensors configured to generate data indicating a speed of the vehicle, fuel levels, engine coolant temperature, engine RPM, throttle position, engine oil temperature, engine fuel rate, intake air temperature, engine runtime, tire pressure, seat occupancy, seat belt engagement, etc.

The infotainment system 212 may serve as a central location for controlling multimedia content for the vehicle, as well as for displaying information to the occupants of the vehicle. For example, the infotainment system may provide routing information by way of a navigation system, audio controls for listening to the radio, mobile device controls for pairing a mobile device with the vehicle, etc. Thus, infotainment system 212 may provide data to the vehicle hub related to which multimedia content is being utilized by an occupant of the vehicle, the identity of any paired mobile devices, as well as current routes utilized by the navigation system.

The powertrain domain 214 may include one or more sensors configured to generate data related to the speed, pressure, position, temperature, status, and/or performance of one or more powertrain related functions of the vehicle, such as the motor engine. In one example, the powertrain domain may generate data indicating a current fuel-efficiency of the motor engine as well as current emissions.

The dashboard domain 216 may include one or more sensors configured to generate data related to the status, state, and/or performance of one or more dashboard related systems of the vehicle. By way of example, the dashboard domain may provide data related to a current position of the steering wheel/column, as well as data related to the current heating/cooling settings of a climate control system of the vehicle.

The in-vehicle sensors 218 may include one or more sensors, such as a motion sensor, a light sensor, a GNSS (e.g., GPS) system, one or more cameras (e.g., an in-cabin camera and/or an external-facing backup or surround-view camera), a breathalyzer, a clock, a microphone, and an engine and/or vehicle sensor connected to any of the in-vehicle networks (e.g., CAN-Bus, LIN, FlexRay, MOST, etc).

In some aspects, a microphone included in the in-vehicle sensors 218 may be utilized by the vehicle hub 220 to generate sound-related data, such as the detection of a baby (or older child) crying, occupants shouting (possibly arguing), loud music from an audio player not connected to the vehicle hub 220 or infotainment system, and/or a barking dog, etc.

In some examples, a motion sensor included in the in-vehicle sensors 218 may be configured to provide movement and/or orientation information which is independent of motion data derived from signals received by the WAN transceiver, the LAN transceiver and the SPS 204. By way of example, the motion sensor may utilize an accelerometer (e.g., a MEMS device), a gyroscope, a geomagnetic sensor (e.g., a compass), an altimeter (e.g., a barometric pressure altimeter), and/or any other type of movement detection sensor, or any combination thereof. Moreover, the motion sensor may include a plurality of different types of devices and combine their outputs in order to provide motion information. For example, the motion sensor may use a combination of a multi-axis accelerometer and orientation sensors to provide the ability to compute positions in 2-D and/or 3-D coordinate systems.

A light sensor included in the in-vehicle sensors 218 may be a rain/light sensor located on or integrated into a windshield of the vehicle and configured to detect the amount of rain and/or light incident onto the vehicle. In another example, the light sensor may be a luminance sensor configured to detect the ambient brightness surrounding the vehicle. In yet another example, the light sensor may be a sensor integrated into the vehicle for the primary purpose of automatically detecting whether to dim the headlights of a vehicle, automatically darkening a rear-view mirror, and/or for automatically adjusting the windshield opacity. In operation, the light sensor is configured to generate one or more light intensity values representative of a lighting condition exterior to the vehicle. In one example, the light intensity value may be in units of lumens. In another example, the light sensor may include a camera, such as a dash-mounted camera, or other forwards-facing camera. A light intensity value may then be derived from one or more images captured by the camera (e.g., average intensity of the one or more images).

The processor 222 of vehicle hub 220 may be communicatively connected to all of the illustrated systems, interfaces, domains, and sensors illustrated in FIG. 2A. The processor 222 may include one or more microprocessors, microcontrollers, and/or digital signal processors that provide processing functions, as well as other calculation and control functionality. Also included in vehicle hub 220 is memory 224 for storing data and software instructions for executing programmed functionality within the vehicle hub 220. The memory 224 may be on-board the processor 222 (e.g., within the same IC package), and/or the memory may be external memory to the processor 222 and functionally coupled over a data bus. The functional details associated with aspects of the disclosure will be discussed in more detail below.

Figure 2B:
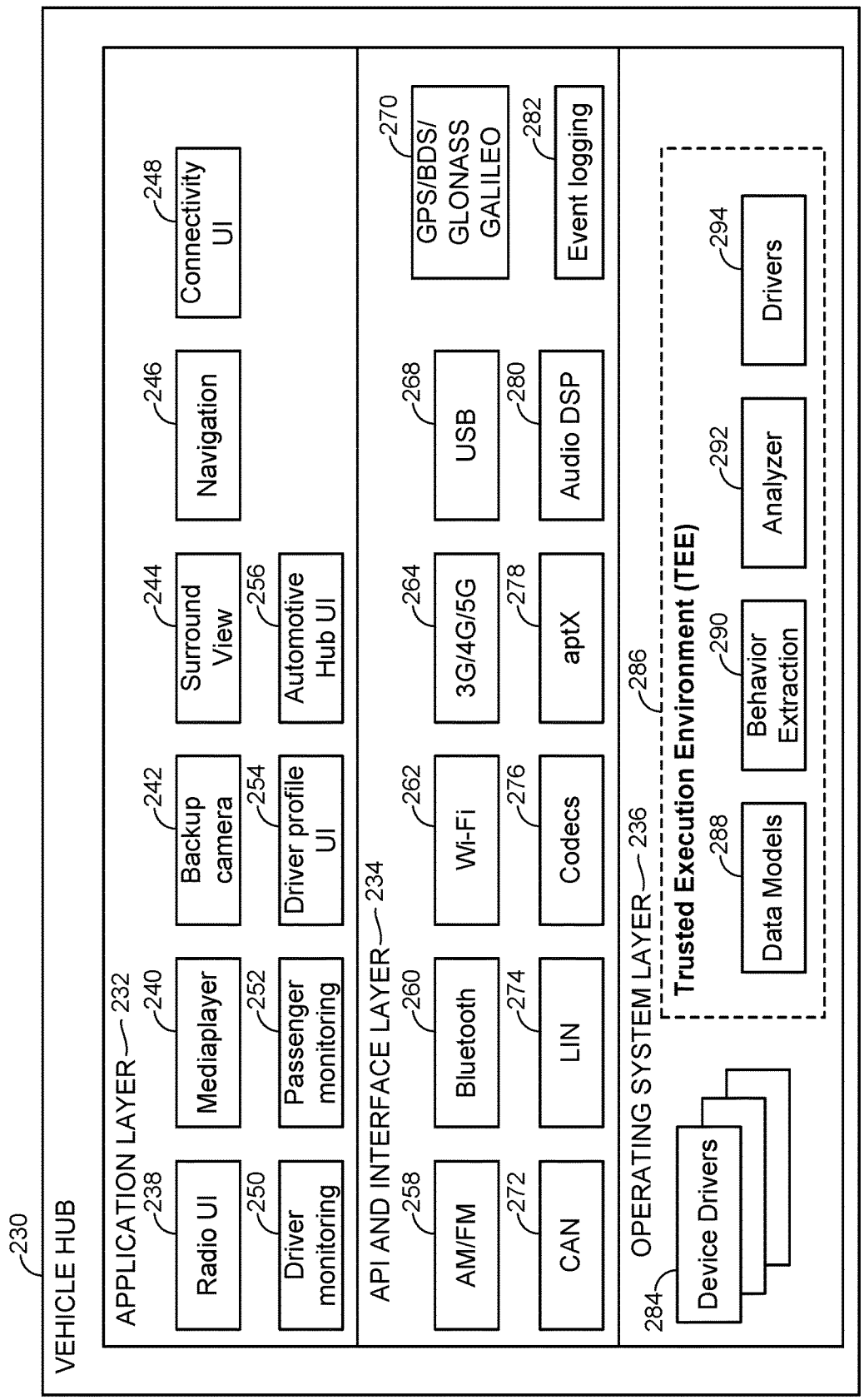
FIG. 2B illustrates an example software layer architecture for a vehicle hub for providing safe-driving support, according to aspects of the disclosure.

FIG. 2B illustrates an example software layer architecture 230 for a vehicle hub for providing safe-driving support, according to aspects of the disclosure. Software layer architecture 230 is one possible architecture implemented via memory 224 of vehicle hub 220 of FIG. 2A.

As shown in FIG. 2B, the software layer architecture 230 may include a number of software layers, such as application layer 232, API and Interface layer 234, and an operating system layer 236. Each software layer may include one or more software modules and data tables that may reside in memory 224 and be utilized by the processor 222 in order to manage both communications and the generating of data. By way of example, the illustrated example of application layer 232 includes a radio user interface (UI) module 238, a mediaplayer module 240, a backup camera module 242, a surround view module 244, a navigation module 246, a connectivity UI module 248, a driver monitoring module 250, a passenger monitoring module 252, a driver profile UI module 254, and an automotive hub UI module 256. The radio UI module 238 may include one or more instructions configured to generate a UI (e.g., via an in-vehicle display) to allow a user (i.e., driver or passenger) to control one or more operations related to broadcast programming such as AM radio broadcast, FM radio broadcast, Satellite broadcast, and/or internet streaming. The mediaplayer module 240 may include one or more instructions configured to generate a UI to allow a user to control one or more operations related to audio and/or video related functions such as playback of a compact disc (CD) or a digital video disc (DVD). The backup camera module 242 may include one or more instructions configured to provide a visual display to a user including video and/or images generated by a backup camera of the vehicle. The surround view module 244 may include one or more instructions configured to provide a visual display to a user including video and/or images generated by one or more surround view cameras of the vehicle. The navigation module 246 may include one or more instructions configured to provide an interface to a user for one or more navigation-related operations such as accepting destination input and/or the display of a navigation route. The connectivity UI module 248 may include one or more instructions configured to provide a user interface for controlling the connection of portable and/or hand-held devices (e.g., USB memory, USB audio/visual devices, Wi-Fi connected devices, Bluetooth connected devices, Ethernet connected devices, etc.) to the vehicle. The driver monitoring module 250 may include one or more instructions configured to generate occupant data related to the driver of the vehicle based on one or more built-in sensors of the vehicle. For example, the driver monitoring module 250 may generate occupant data related to the driver based on a seat-belt monitor, one or more cameras (e.g., facial recognition, eye-tracking, etc.), a breathalyzer, and/or through the detection of a mobile-device that is present in or near the vehicle (e.g., driver monitoring module 250 may detect the presence of a mobile device based on data received from the connectivity UI module 248). The passenger monitoring module 252 may include one or more instructions configured to generate occupant data related to a passenger of the vehicle based on one or more built-in sensors of the vehicle. For example, the passenger monitoring module 252 may generate occupant data related to the passenger based on a seat-belt monitor, one or more cameras (e.g., facial recognition, eye-tracking, infant car seat detection, pet detection etc.), and/or through the detection of a mobile-device that is present in or near the vehicle (e.g., passenger monitoring module 252 may detect the presence of a mobile device based on data received from the connectivity UI module 248).

The driver profile UI module 254 may include one or more instructions configured to operate in a data input mode as well as a driver identification mode. The data input mode may include the driver profile UI module 254 allowing user input for the a priori identification of a driver, such as through facial recognition, association with an identified mobile device, etc. In one example, a user profile may be generated for a specific individual driver based on the user input. The user profile may also be assigned to one of a plurality of pre-determined categories of user profiles, such as an 'adult driver', a 'teenage driver,' and a 'senior-citizen driver' based on input received from the user. During normal operations, the driver identification mode may include one or more instructions configured to automatically identify the driver and the associated user profile based on data received when the driver is located in or near the vehicle. For example, the driver identification mode may identify the driver based on facial recognition via one or more cameras, via a personal identification number (PIN) entered by the driver, and/or via the detection of a mobile device associated with the driver. In one aspect, the driver identification mode may also identify the driver based on one or more verification questions presented to driver via a display and/or via an audio system of the vehicle. For example, the driver profile UI module 254 may ask the driver questions related to past driving activities of the vehicle, such as "Which place of business did you visit the day before yesterday?", "Which favorite location did you last specify as a destination for the navigation console?", "How many were in this vehicle when you last visited the supermarket?", or "Where was the last place you visited besides home and work?" In one aspect, the verification questions may be dynamically generated by the driver profile UI module 254 based on past driving activities associated with each of the driver profiles. The driver profile UI module 254 may then communicate with analyzer module 292 (discussed below) to identify and/or verify the identity of the driver based on the driver's answer to these questions. In some aspects, the driver may provide answers to the verification questions via voice-recognition and/or via text or other input on a touch-screen display of the vehicle.

Further shown as included in the application layer 232 is an automotive hub UI module 256. As mentioned above, aspects of the present disclosure include the leveraging of data collected at the vehicle hub 220 for promoting a safe-driving experience, where action data is generated by applying the data to a machine-learning safe-driving model. The action data relates to an action that is to be performed by the vehicle in order to improve the safe-driving of the vehicle. Accordingly, the automotive hub UI module 256 may include one or more instructions for performing an action based on the action data. In one aspect, the automotive hub UI module 256 may interact with one or more of the illustrated modules 238-254 to perform an action based on the action data. By way of example, the automotive hub UI module 256 may interact with the radio UI module 238 and/or the mediaplayer module 240 to restrict the volume and/or programming of a radio of the vehicle. In another example, the automotive hub UI module 256 may interact with the navigation module 246 to provide specific routes and/or routing limitations based on the action data (e.g., no freeways for senior citizen drivers, prefer well-lit routes at night for senior citizen drivers, traffic avoidance preferences, avoidance of routes under repair when passengers include infants, etc.). In yet another example, the automotive hub UI module 256 may interact with the connectivity UI module 248 to restrict network access by a mobile device.

With regards to the API and Interface layer 234, this layer may include various modules 258-282 that include instructions, subroutines, protocols, and/or tools for enabling communication between various software components. In one aspect, the modules 258-282 are configured to enable communication between the modules 238-256 of the application layer 232 and the operating system layer 236. For example, operating system layer 236 may include one or more device drivers 284 that are configured to include hardware-specific instructions. Thus, the AM/FM module 258 may include one or more instructions to enable communication between the radio UI module 238 and a device driver 284 that is specific to an AM radio receiver, an FM radio receiver, a satellite radio receiver, and/or an internet streaming receiver (e.g., a modem). The Bluetooth module 260 may include one or more instructions to enable communication between one or more modules of the application layer 232 (e.g., media player module 240 and/or connectivity UI module 248) and a device driver 284 that is specific to a Bluetooth transceiver according to one or more Bluetooth versions (e.g., Bluetooth 3.0 and earlier, and/or Bluetooth Low Energy). The Wi-Fi module 262 may include one or more instructions to enable communication between one or more modules of the application layer 232 (e.g., navigation module 246 and/or mediaplayer module 240) and a device driver 284 that is specific to a Wi-Fi transceiver. The 3G/4G/5G module 264 may include one or more instruction to enable communication between one or more modules of the application layer 232 (e.g., automotive hub UI module 256) and a device driver 284 that is specific to a wireless transceiver that is configured to communication with one or more commercial telephone networks. The USB module 268 may include one or more instructions that are configured to enable communication between one or more modules of the application layer 232 (e.g., connectivity UI module 248) and a device driver 284 that is specific to a USB interface for direct wired connections (e.g., to external memory and/or to external devices). The GPS module 270 may include one or more instructions that are configured to enable communication between one or more modules of the application layer 232 (e.g., navigation module 246) and a device driver 284 that is specific to one or more navigation systems such as GPS (global positioning system), BDS (BeiDou Navigation Satellite System), GLONASS (Global Navigation Satellite System), and Galileo. In one aspect, the GPS module 270 may include one or more interfaces and/or communicate with SPS receiver 204 of FIG. 2A.

The API and Interface layer 234 may further include one or more modules that include instructions that are configured to enable communication with one or more in-vehicle networks (IVNs) to provide access to sensors and/or actuators of the vehicle. For example, the illustrated example of API and Interface layer 234 is shown as including a controller area network (CAN) module 272 and a local interconnect network (LIN) module 274. However, other modules not illustrated may also be included in the API and Interface layer 234 for enabling communication with one or more other IVNs, such as Media-Oriented Systems Transport (MOST), Flexray, etc.

The Codecs module 276 may include one or more instructions that are configured for the encoding of analog and/or digital signals for network interconnections such as Wi-Fi, Bluetooth, and/or GPS. The aptX module 278 may include one or more instructions that are configured to enhance audio signal quality over Bluetooth communications. The Audio DSP module 280 may include one or more instructions that are configured to perform digital signal processing for audio signals. In another example, the Audio digital signal processing (DSP) module 280 may include instructions that are configured to enable communication between one or more modules of the application layer 232 and a device driver 284 that is specific for a digital signal processor implemented in hardware.

The event logging module 282 may be implemented as a combination of API and network message logging. For example, the event logging module 282 may be configured to monitor communication between one or more modules of the application layer 232 and the operating system layer 236. The event logging module 282 may collect these communications and log events that are significant for one or more machine learning safe-driving models. For example, the event logging module 282 may monitor communication between the connectivity UI module 248 and a device driver 284 and log an event such as the pairing of a mobile device with the vehicle.

Turning now to the operating system layer 236 in more detail, this layer includes one or more device drivers 284 (discussed above) as well as a trusted execution environment (TEE) 286. The TEE 286 is shown as including one or more data models module 288, a behavior extraction module 290, an analyzer module 292, and one or more device drivers 294. In one aspect, the data models module 288 may store machine learning safe-driving models received from a server (e.g., safe-driving server 170 of FIG. 1). The behavior extraction module 290 is configured to receive a heterogeneous stream of events from the event logging module 282 and to recognize abstract behaviors in response thereto. For example, the behavior extraction module 290 may receive a stream of events from the event logging module 282 such as vehicle speed, vehicle lane departures, image captures of the driver, and to recognize an unsafe driving behavior of the driver (e.g., due to driver drowsiness). As will be discussed in more detail below, the analyzer module 292 may be configured to identify an occupant of the vehicle based on the occupant data and may also be configured to apply locally-stored machine-learning safe-driving models to the occupant and vehicle data to generate action data. The device drivers 294 may include one or more instructions specific for execution of the TEE 286. For example, the device drivers 294 may include one or more instructions that are configured for transmitting event logs (e.g., those generated by event logging module 282) to a server (e.g., safe-driving server 170 of FIG. 1).

In one aspect the TEE 286 is an operating system infrastructure that includes encryption to resist or otherwise prevent tampering with the programs and/or modules under its control. The organization of the memory contents as shown in FIG. 2B is merely exemplary, and as such the functionality of the modules and/or data structures may be combined, separated, and/or be structured in different ways depending upon the implementation of the vehicle hub 220.

Referring now back to FIG. 2A, vehicle hub 220 is configured to receive occupant data and vehicle data via one or more of the sensors, interfaces, domains, and/or systems illustrated in FIG. 2A and to transmit the occupant and vehicle data to the safe-driving server 170. In one aspect, the occupant data is related to an identity and health status of an occupant of the vehicle and the vehicle data is related to a status of the vehicle. For example, the occupant data related to the identity of the occupant may include an image of the occupant, a finger print of the occupant, data identifying the mobile device located within the vehicle, data indicating a position of a vehicle seat of the vehicle, data indicating a position of a steering wheel of the vehicle, and/or data indicating a current multimedia activity of the occupant. The occupant data related to the health status of the occupant may include an image of the occupant, data received at the vehicle hub from a bio-sensor located within the vehicle, data indicating a blood alcohol content of the occupant, data indicating a blood pressure of the occupant, and/or data indicating a heart rate of the occupant. In some examples, the occupant data relates to any occupant of the vehicle and may include the driver, a passenger, or occupant data related to both the driver and passenger. Thus, in some aspects of the present disclosure, safe-driving support may be determined based, in part, on the identity of the driver itself, based on the identity of the passenger itself, or based on a combination of the identity of the driver and passengers (e.g., teenage driver with teenage passengers vs. teenage driver with parent passengers).

The vehicle data may include data indicating a current location of the vehicle, data indicating a current time, data indicating a current date, data indicating a speed of the vehicle, and/or data indicating a current state or diagnostics of one of more domains of the vehicle, as mentioned above.

In some implementations, the vehicle hub 220 is configured to continuously generate and transmit the occupant data and vehicle data to the safe-driving server 170, both as soon as an occupant enters the vehicle and as the vehicle travels through an operating environment 100. In other implementations, the vehicle hub 220 is configured to continuously collect the occupant data and vehicle data, but to only periodically transmit the data to the safe-driving server 170. For example, the vehicle hub 220 may collect and store occupant data and vehicle data in memory 224, where the occupant data and vehicle data stored in the memory 224 may be uploaded to the safe-driving server 170 according to a predetermined schedule or when network connectivity becomes available.

Figure 3:
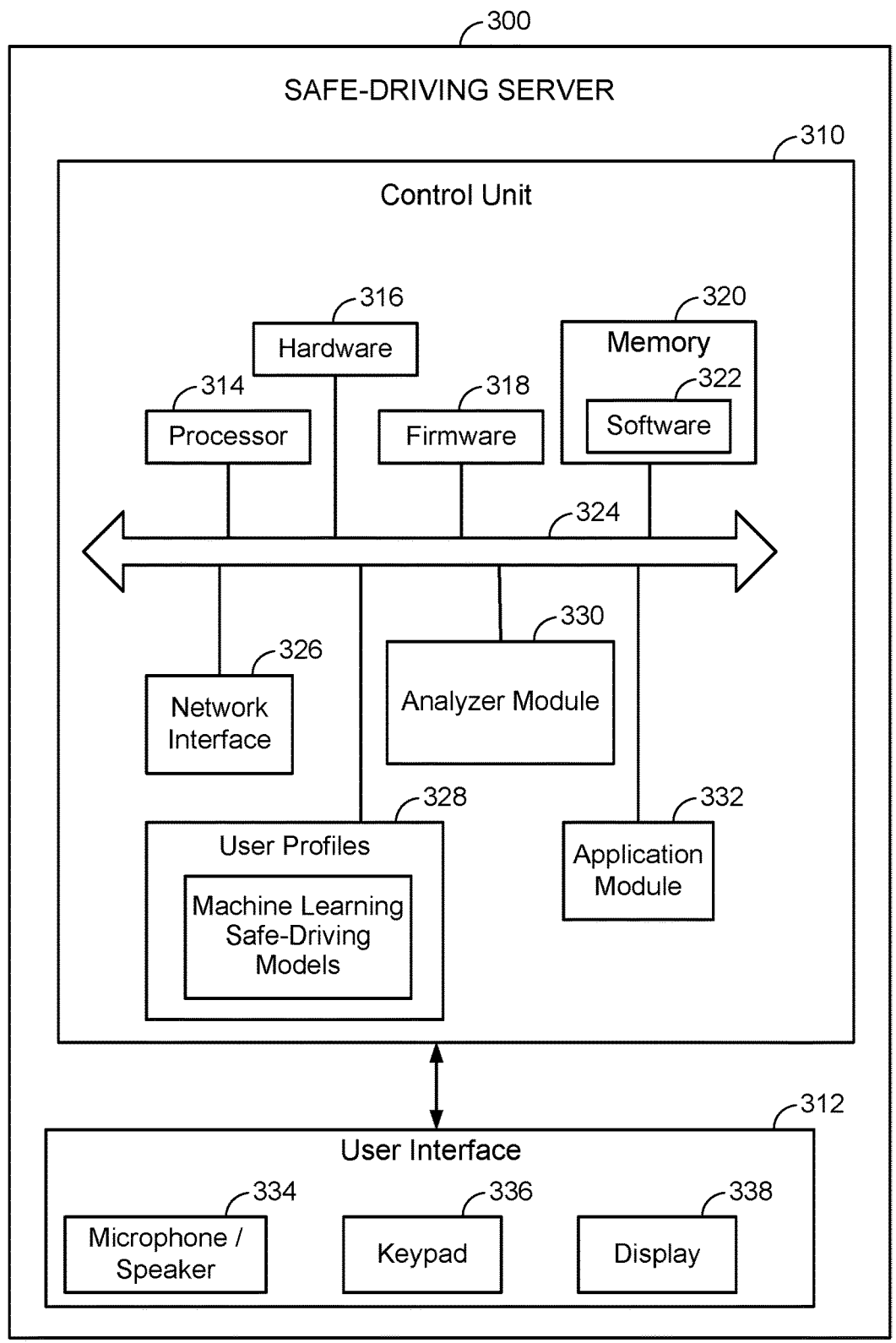
FIG. 3 illustrates an example safe-driving server for providing safe-driving support, according to aspects of the disclosure.

FIG. 3 illustrates an example safe-driving server 300 for providing safe-driving support, according to aspects of the disclosure. Safe-driving server 300 is one possible implementation of safe-driving server 170 of FIG. 1.

The various features and functions illustrated in the diagram of FIG. 3 are connected together using a common data bus 324 which is meant to represent that these various features and functions are operatively coupled together. Those skilled in the art will recognize that other connections, mechanisms, features, functions, or the like, may be provided and adapted as necessary to operatively couple and configure an actual portable device. Further, it is also recognized that one or more of the features or functions illustrated in the example of FIG. 3 may be further subdivided or two or more of the features or functions illustrated in FIG. 3 may be combined.

Safe-driving server 300 includes a control unit 310 that is configured to receive occupant data and vehicle data from a plurality of vehicles via network interface 326. Control unit 310 may be provided by a processor 314 and associated memory 320, hardware 316, firmware 318, and software 322.

The processor 314 may include one or more microprocessors, microcontrollers, and/or digital signal processors that provide processing functions, as well as other calculation and control functionality. The processor 314 may also include memory 320 for storing data and software instructions for executing programmed functionality within the safe-driving server 300. The memory 320 may be on-board the processor 314 (e.g., within the same IC package), and/or the memory may be external memory to the processor 314 and functionally coupled over a data bus 324. The functional details associated with aspects of the disclosure will be discussed in more detail below.

Control unit 310 may further include user profiles 328, an analyzer module 330, and an application module 332. The user profiles 328 include a plurality of user profiles, each including an associated machine learning safe-driving model. During operation, the analyzer module 330 may identify a user profile corresponding to an occupant of the vehicle from among the user profiles 328 based on the occupant data received from the vehicle hub 220. In one aspect, analyzer module 330 includes and utilizes a machine learning user identification model to identify the user profile from among the user profiles 328. After identifying the user profile corresponding to the occupant of the vehicle, the analyzer module 330 may then apply the occupant data and vehicle data to the corresponding machine learning safe-driving model associated with the user profile. In one aspect, applying the occupant data and the vehicle data to the machine learning safe-driving model results in the generation of one or more action data. The action data relates to an action to be performed by the vehicle in order to improve the safe driving of the vehicle. The action data is then transmitted back to the vehicle hub 220 for the vehicle hub to perform the action. In some aspects, performing the action based on the action data may include the vehicle implementing a parental control related to the occupant of the vehicle, limiting cellular data access of a mobile device located within the vehicle, disabling of text messaging by the mobile device, limiting multimedia content available by an infotainment system of the vehicle, deactivating an engine of the vehicle, limiting a speed of the vehicle, providing a route via a navigation system of the vehicle, or providing a safe-driving recommendation (e.g., alert) to a driver of the vehicle.

The application module 332 may be a process running on the processor 314, which provides an interface/mechanism for a user to create one or more user profiles for storage in user profiles 328. These applications typically run within an upper layer of the software architectures, and may include software for interacting with user interface 312 and/or for communicating with a vehicle hub 220.

Processor 314, analyzer module 330, and application module 332 are illustrated separately for clarity, but may be a single unit and/or implemented in the processor 314 based on instructions in the software 322 which is run in the processor 314. Processor 314, analyzer module 330, and application module 332 can, but need not necessarily include, one or more microprocessors, embedded processors, controllers, application specific integrated circuits (ASICs), digital signal processors (DSPs), and the like. The term processor describes the functions implemented by the system rather than specific hardware. Moreover, as used herein the term "memory" refers to any type of computer storage medium, including long term, short term, or other memory associated with safe-driving server 300, and is not to be limited to any particular type of memory or number of memories, or type of media upon which memory is stored.

The processes described herein may be implemented by various means depending upon the application. For example, these processes may be implemented in hardware 316, firmware 318, processor 314 in combination with software 322, or any combination thereof. For a hardware implementation, the processor 314 may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a firmware and/or processor/software implementation, the processes may be implemented with modules (e.g., procedures, functions, and so on) that perform the functions described herein. Any non-transitory computer-readable medium tangibly embodying instructions may be used in implementing the processes described herein. For example, program code may be stored in memory 320 and executed by the processor 314. Memory 320 may be implemented within or external to the processor 314.

If implemented in firmware 318 and/or processor 314 with software 322, the functions may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise Random Access Memory (RAM), Read-Only Memory (ROM), Flash Memory, Electrically Erasable Programmable Read Only Memory (EEPROM), Compact Disc Read-Only Memory (CD-ROM) or other optical disk storage, magnetic disk storage or other magnetic storage devices, or any other medium that can be used to store desired program code in the form of instructions or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. As used herein, a computer-readable media may also include a secure digital (SD) card, universal serial bus (USB) memory stick, or a solid state drive (SSD). Combinations of the above should also be included within the scope of computer-readable media.

The safe-driving server 300 may include an optional user interface 312 which provides any suitable interface systems, such as a microphone/speaker 334, keypad 336, and display 338 that allows user interaction with the safe-driving server 300. The microphone/speaker 334 provides for audible alerts to be presented to a user. The keypad 336 comprises any suitable buttons for user input. The display 338 comprises any suitable display, such as, for example, a backlit Liquid Crystal Display (LCD) display, and may further include a touch screen display for additional user input modes.

Figure 4:
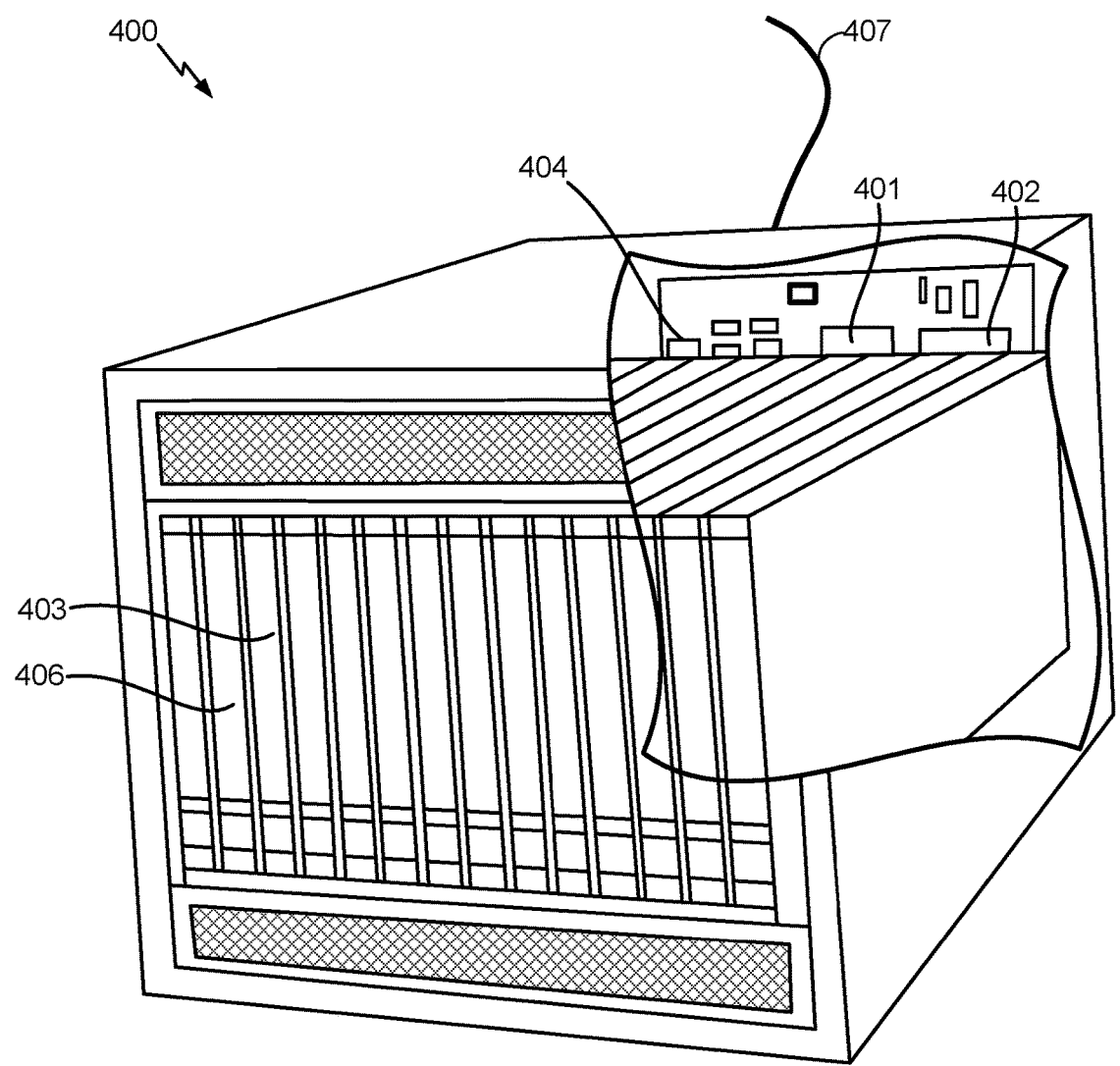
FIG. 4 illustrates a server in accordance with one aspect of the disclosure.

The various embodiments of safe-driving server 170 and/or 300 may be implemented on any of a variety of commercially available server devices, such as server 400 illustrated in FIG. 4. In an example, the server 400 may correspond to one example configuration of the safe-driving server 300 described above. In FIG. 4, the server 400 includes a processor 401 coupled to volatile memory 402 and a large capacity nonvolatile memory, such as a disk drive 403. The server 400 may also include a one or more SD cards, USB drives, SSDs, a floppy disc drive, CD or DVD disc drive 406 coupled to the processor 401. The server 400 may also include network access ports 404 coupled to the processor 401 for establishing data connections with a network, either wirelessly or via a wired-connection 407, such as a local area network coupled to other broadcast system computers and servers or to the Internet. In context with FIG. 3, it will be appreciated that the server 400 of FIG. 4 illustrates one example implementation of the safe-driving server 300, whereby the server 400 includes logic configured to receive occupant data and vehicle data from a plurality of vehicles, where such logic may be included within or at network access ports 404 used by the server 400 to communicate with the network, either wirelessly or via wired-connection 407. The server 400 may also include logic configured to identify a user profile based on the occupant data and to apply the occupant data and vehicle data to a machine learning safe-driving model, which may correspond to processor 401 along with any combination of the volatile memory 402, the disk drive 403 and/or the disc drive 406.

Figure 5A:
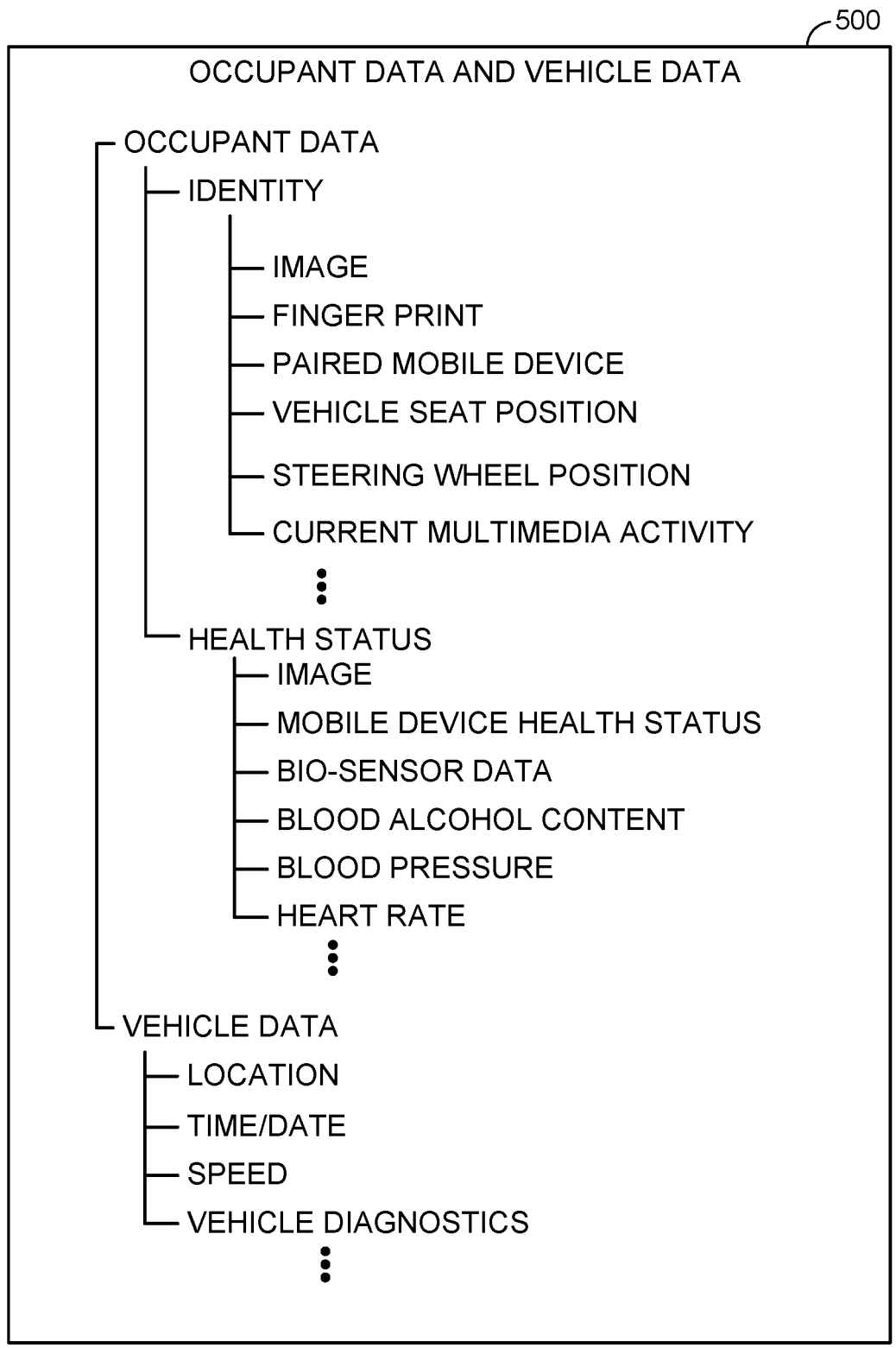
FIG. 5A illustrates an example occupant data and vehicle data, according to aspects of the disclosure.

FIG. 5A illustrates an example occupant data and vehicle data 500, according to aspects of the disclosure. Occupant data and vehicle data 500 is one possible implementation of data generated by the vehicle hub 220 of FIG. 2A. As shown in FIG. 5A, the occupant data and vehicle data 500 may include both occupant data related to the identity and health status of an occupant of the vehicle as well as vehicle data related to a status of the vehicle. As discussed above, the occupant data may refer to the driver and/or a passenger of the vehicle. The occupant data related to the identity of the occupant may include an image of the occupant, a finger print of the occupant, data identifying a mobile device located within the vehicle (e.g., a paired mobile device), data indicating a position of a vehicle seat of the vehicle, data indicating a position of a steering wheel of the vehicle, data indicating a current multimedia activity of the occupant, etc.

The occupant data related to the health status of the occupant may include data related to the health status of the occupant received at the vehicle hub from the mobile device located within the vehicle, an image of the occupant, data received at the vehicle hub from a bio-sensor located within the vehicle, data indicating a blood alcohol content of the occupant, data indicating a blood pressure of the occupant, data indicating a heart rate of the occupant, etc.

In one aspect, the vehicle data is obtained by the vehicle hub from an in-vehicle sensor, a mobile device located within the vehicle, a stationary monitor exterior to the vehicle, or another vehicle proximate to the vehicle. The vehicle data may include data indicating a current location of the vehicle, data indicating a current time, data indicating a current date, data indicating a speed of the vehicle, data indicating a current diagnostics of one of more vehicle domains of the vehicle (e.g., the domains 202-218 of FIG. 2A).

Figure 5B:
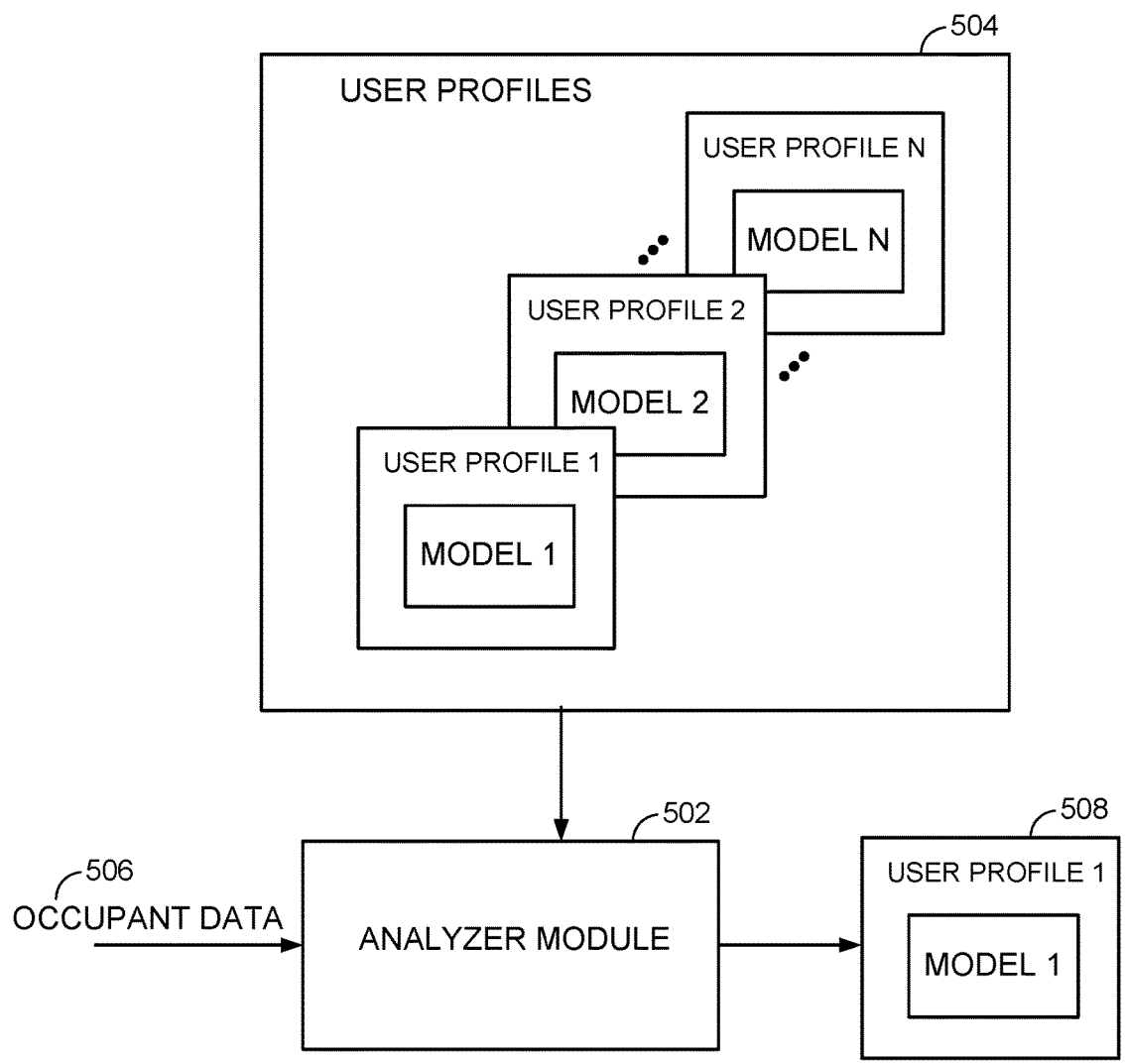
FIG. 5B illustrates an example identification of a user profile from among several user profiles based on occupant data, according to aspects of the disclosure.

FIG. 5B illustrates an example identification of a user profile 508 from among several user profiles 504 based on occupant data 506, according to aspects of the disclosure. In some aspects, the vehicle hub 220 is configured to wirelessly transmit occupant data (e.g., see FIG. 5A) to a server, such as safe-driving server 170 of FIG. 1 when an occupant enters a vehicle, where the server is then configured to identify the occupant and a user profile associated with the occupant. In this case, the analyzer module 502 may correspond to the analyzer module 330 of FIG. 3. In other examples, the vehicle hub 220, itself, may be configured to identify the occupant of the vehicle locally based on the occupant data gathered by the vehicle hub 220. Thus, the analyzer module 502 of FIG. 5B may also correspond to analyzer module 292 of FIG. 2B.

In operation, the analyzer module 502 is configured to obtain the occupant data 506, such as the occupant data illustrated in FIG. 5A. As described above, the occupant data 506 may relate to an identity of the occupant, such as an image of the occupant, a finger print, a paired mobile device, vehicle seat position, steering wheel position, and/or a current multimedia activity of the infotainment system 212. In some aspects, the analyzer module 502 is configured to perform a multi-factor authentication to verify the identity of the occupant. For example, the analyzer module 502 may identify the occupant based on a white list of known drivers, an association of the vehicle hub with an occupant's mobile device, an occupant's wearable device, in-vehicle activities (types of multimedia services used by the occupant, applications used by the occupant, etc.), static information (e.g., occupant defined pin and/or pass codes entered via driver profile UI 254), and/or dynamic information such as the occupant answers to one or more questions presented by the driver profile UI module 254 when in the driver identification mode (e.g., Did you go to the office on Friday?, Did you take freeway 101 yesterday?, Where did you go yesterday? Which apps did the driver and passenger use?).

In some aspects, the analyzer module 502 may include a machine learning user identification model to identify the user profile from among the user profiles 328. The machine learning user identification model may represent a model of the identity of an occupant upon which one of the user profiles 1-N may be selected from plurality of user profiles 504. For example, the machine learning user identification model may include performing an analysis technique such as a machine learning technique or other advanced technique for data analysis. The machine learning technique may be a supervised, unsupervised, or a reinforcement learning technique. As shown in the example of FIG. 5B, the analyzer module 502 determines the identity of an occupant of the vehicle associated with user profile 1 508 based on the obtained occupant data 506.

Figure 5C:
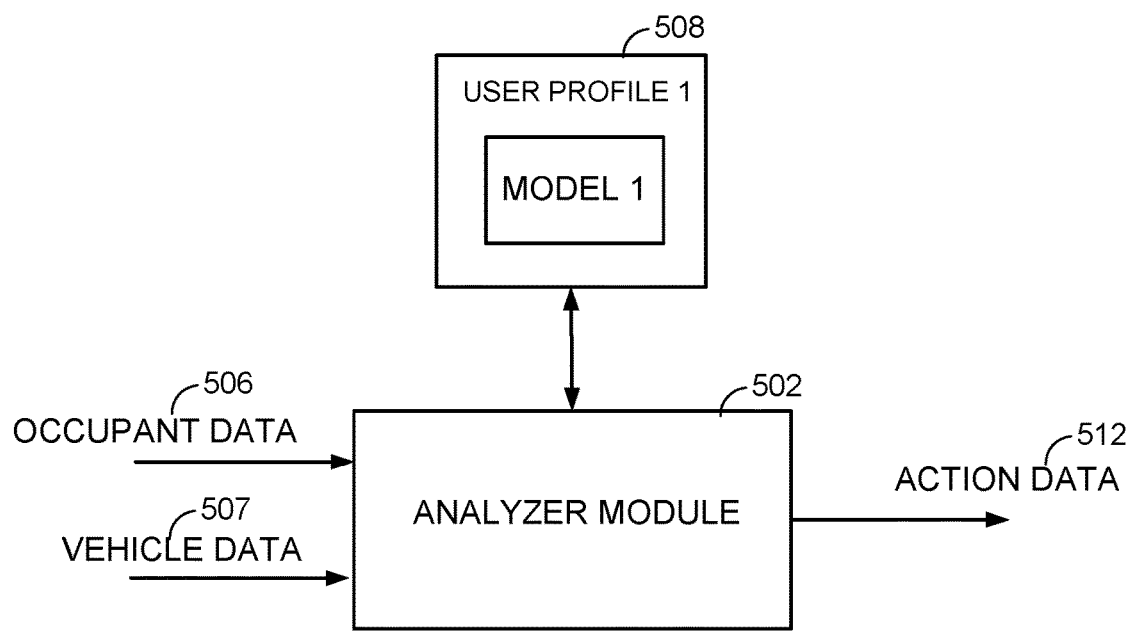
FIG. 5C illustrates another example application of occupant data and vehicle data to a machine learning safe-driving model to obtain action data, according to aspects of the disclosure.

FIG. 5B further illustrates that each of the user profiles 1-N has an associated machine learning safe-driving model (e.g., models 1-N). As will be described below each of the machine learning safe-driving models 1-N may represent a model of driving and/or occupant activity upon which action data may be generated that are specific to a particular occupant. For example, FIG. 5C illustrates the application of occupant data 506 and vehicle data 507 to the machine learning safe-driving model 1 of user profile 508 to obtain action data 512.

Figure 6A:
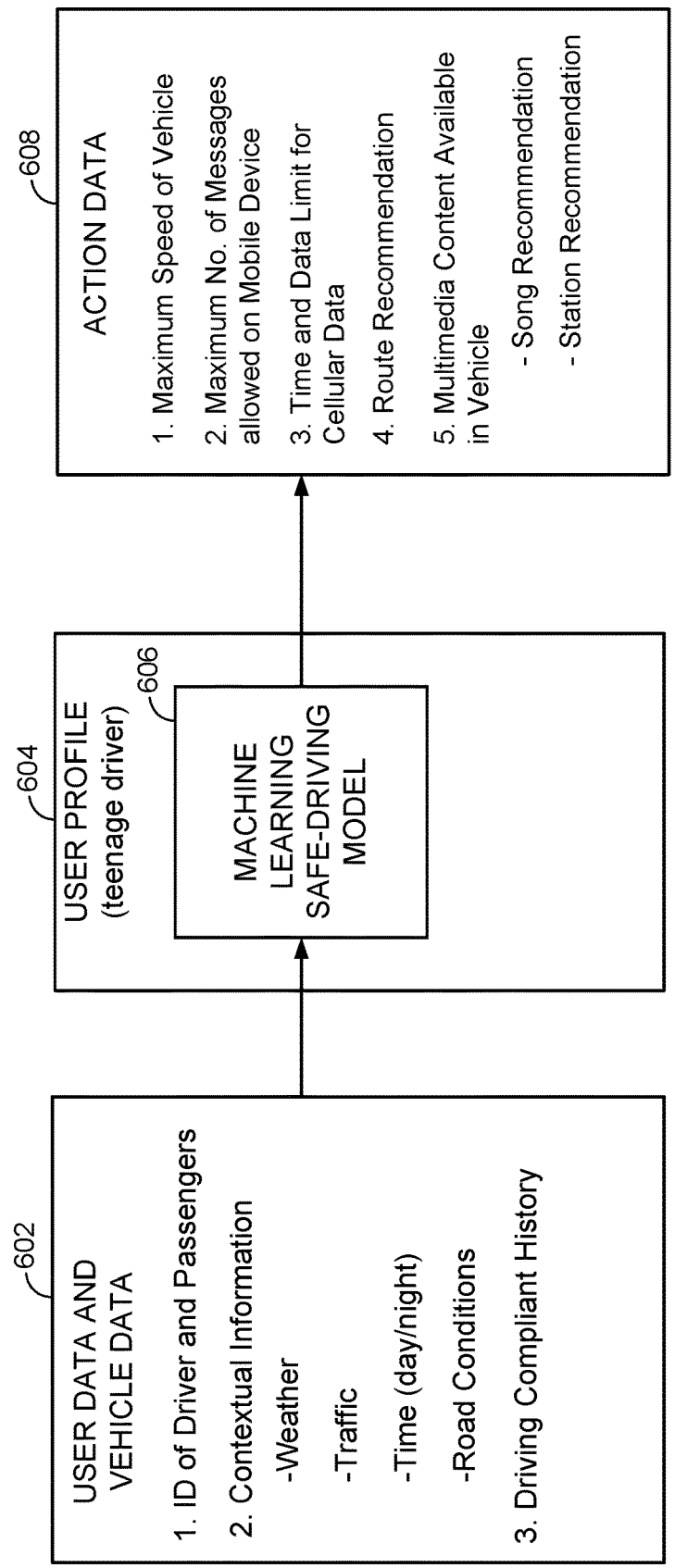
FIG. 6A illustrates an example application of occupant data and vehicle data to a machine learning safe-driving model associated with a teenage driver user profile in order to obtain action data, according to aspects of the disclosure.

FIG. 6A illustrates an example application of occupant data and vehicle data 602 to a machine learning safe-driving model 606 associated with a teenage driver user profile 604 in order to obtain action data 608, according to aspects of the disclosure. As shown in FIG. 6A relevant user data and vehicle data 602 for use in application to the machine learning safe-driving model 606 may include the identification of the driver as well as the identification of any passengers that are currently in the vehicle. Additional user data and vehicle data 602 may include contextual information such as the current weather, traffic conditions, the time of day, and/or current road conditions. Further relevant user data and vehicle data 602 may include a driving compliant history of the driver (e.g., vehicle speed relative to the speed limit, occurrences of lane departures, etc.). The analyzer module 502 may then apply the occupant data and vehicle data 602 to the machine learning safe-driving model 606 associated with user profile 604 to generate the action data 608. As shown in FIG. 6A, the action data 608 may include one or more actions to be performed by the vehicle, such as limiting a maximum speed of the vehicle, limiting the number of messages allowed on one or more mobile devices located within the vehicle, providing a time and/or data limit for cellular data, providing a route recommendation, and/or limiting or only providing specific multimedia content available in the vehicle. As is apparent the action data 608 provided is dependent on the machine learning safe-driving model specific to the associated user profile 604. That is, in some implementations the same user data and vehicle data 602 may yield different action data 608 when applied to a machine learning safe-driving model of a different user profile (e.g., an adult user profile may result in less restrictive action data when compared to a teenage user profile).

Figure 6B:
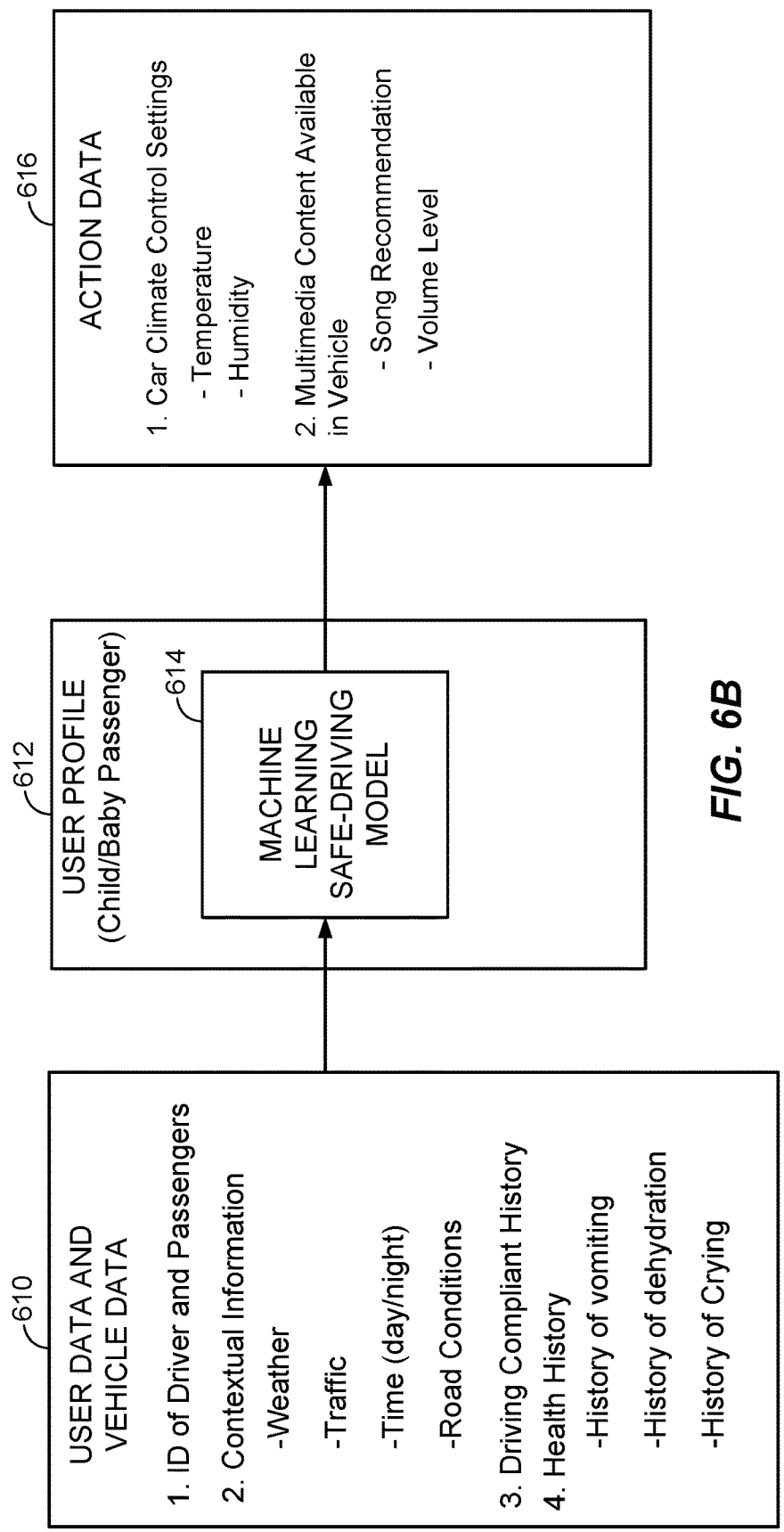
FIG. 6B illustrates an example application of occupant data and vehicle data to a machine learning safe-driving model associated with a child/baby passenger user profile in order to obtain action data, according to aspects of the disclosure.

FIG. 6B illustrates an example application of occupant data and vehicle data 610 to a machine learning safe-driving model 614 associated with a child/baby passenger user profile 612 in order to obtain action data 616, according to aspects of the disclosure. As shown in FIG. 6B relevant user data and vehicle data 610 for use in application to the machine learning safe-driving model 614 may include the identification of the driver as well as the identification of any passengers that are currently in the vehicle. Additional user data and vehicle data 610 may include contextual information such as the current weather, traffic conditions, the time of day, and/or current road conditions. Further relevant user data and vehicle data 602 may include a driving compliant history of the driver (e.g., vehicle speed relative to the speed limit, occurrences of lane departures, etc.). In addition, the user data and vehicle data 610 may include health history of the child passenger, such as a history of vomiting, a history of dehydration, and/or a history of crying. In this context, the health history of the child passenger may refer to health history during the current journey/trip (i.e., not previous journeys/trips) and may include current health data as well. Thus, in one aspect, the health history of the child passenger may include health data collected over a period of time for the current journey/trip. The analyzer module 502 may then apply the occupant data and vehicle data 610 to the machine learning safe-driving model 614 associated with user profile 612 to generate the action data 616. As shown in FIG. 6B, the action data 616 may include one or more actions to be performed by the vehicle, such as controlling one or more vehicle climate settings, such as temperature and/or humidity. In addition, the action data 616 may control the multimedia content available in the vehicle, such as by adjusting a volume level and/or providing a song recommendation (e.g., children's music, soothing music, etc.).

Figure 7:
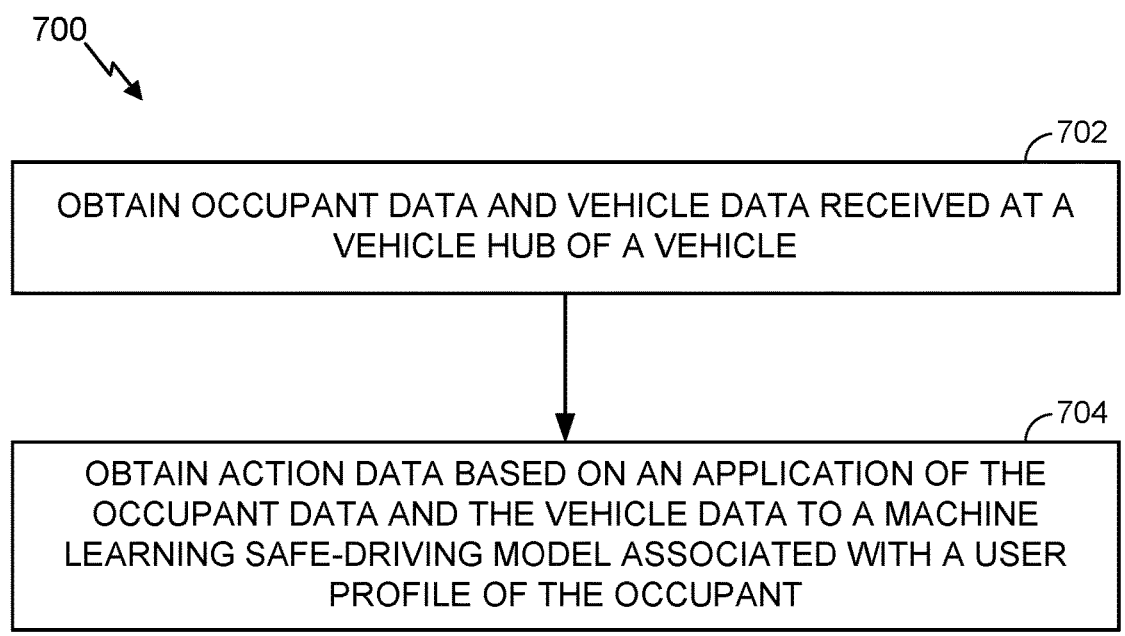
FIG. 7 is a flowchart illustrating a process of providing safe-driving support of a vehicle, according to aspects of the disclosure.

FIG. 7 is a flowchart illustrating a process 700 of providing safe-driving support of a vehicle, according to aspects of the disclosure. Process 700 is one example process that may be performed by vehicle platform 200 of FIG. 2A or by safe-driving server 300 of FIG. 3. In process block 702, an analyzer module obtains occupant data and vehicle data that was received at a vehicle hub of the vehicle. For example, FIG. 5C illustrates an analyzer module 502 as obtaining occupant data 506 and vehicle data 507, where the occupant data 506 and vehicle data 507 were received at a vehicle hub, such as vehicle hub 220 of FIG. 2A. As described above, the occupant data 506 is related to an identity and health status of an occupant of the vehicle and the vehicle data 507 is related to a status of the vehicle. Next, process block 704 includes obtaining action data based on an application of the occupant data and vehicle data to a machine learning safe-driving model. As shown in FIG. 5B, the analyzer module 502 may identify one user profile (e.g., user profile 1 508) from among a plurality of user profiles 504, where the machine learning safe-driving model is one of a plurality of machine learning safe-driving models (e.g., Models 1-N), each associated with a respective one of the user profiles 1-N. As further shown in FIG. 5C, the analyzer module 502 applies the occupant data 506 and the vehicle data 507 to the identified machine learning safe-driving model of user profile 1 508 to generate the action data 512. As discussed above, the action data 512 relates to an action to be performed by the vehicle while the occupant is located in the vehicle.

Figure 8:
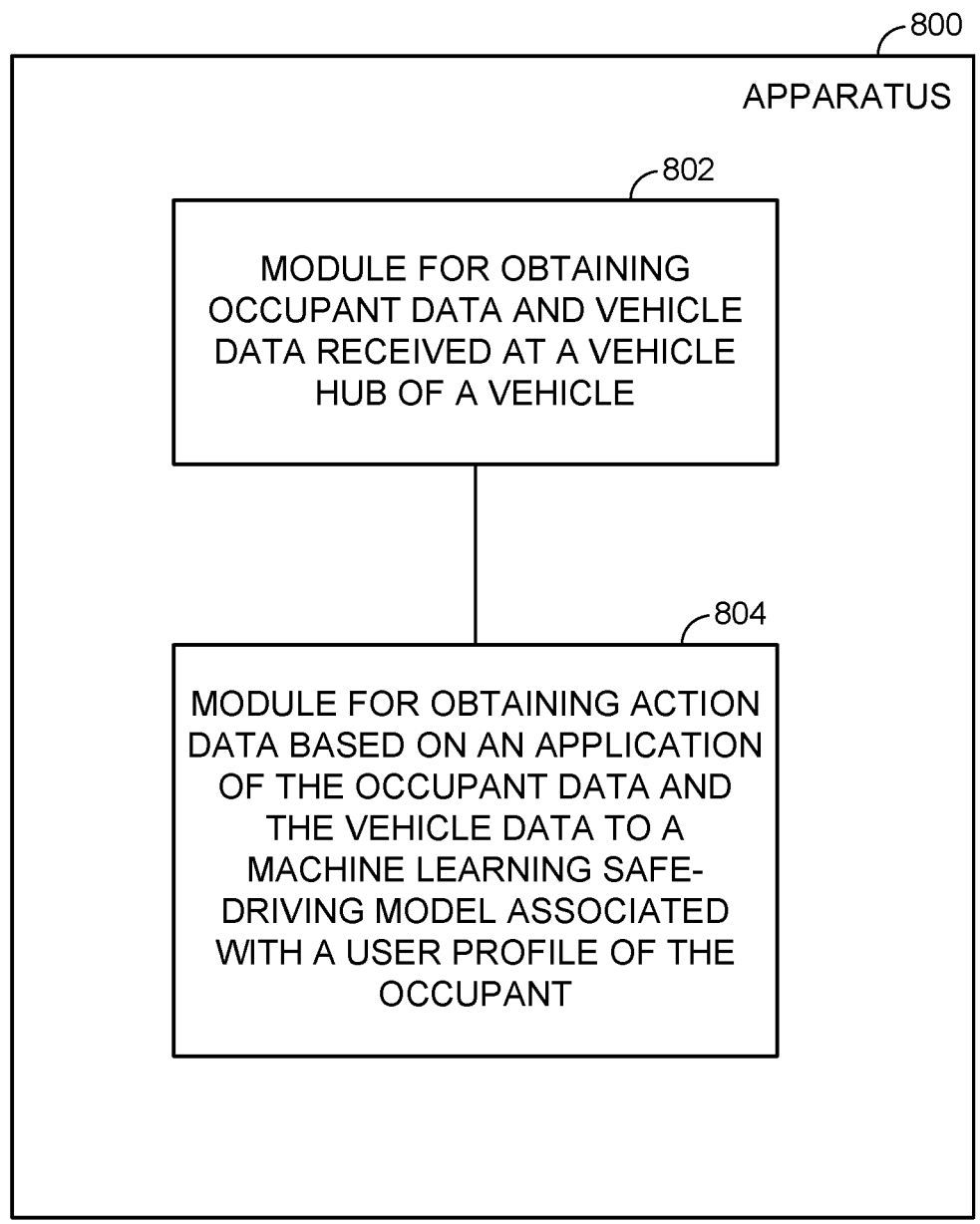
FIG. 8 illustrates several sample aspects of components that may be employed in an apparatus configured to provide safe-driving support, according to aspects of the disclosure.

FIG. 8 illustrates several sample aspects of components that may be employed in an apparatus 800 configured to provide safe-driving support, according to aspects of the present disclosure. Apparatus 800 is one possible implementation of vehicle hub 220 of FIG. 2A and/or safe-driving server 300 of FIG. 3. A module 802 for obtaining occupant data and vehicle data received at a vehicle hub of a vehicle may correspond at least in some aspects to, for example, the processor 222 and/or memory 224 of vehicle hub 220 of FIG. 2A, the analyzer module 292 of FIG. 2B, the processor 314, memory 320, and/or analyzer module 330 of control unit 310 of FIG. 3, and/or the analyzer module 502 of FIGS. 5B and 5C. A module 804 for obtaining action data based on an application of the occupant data and the vehicle data to a machine learning safe-driving model may correspond at least in some aspects to, for example, the processor 222 and/or memory 224 of vehicle hub 220 of FIG. 2A, the analyzer module 292 of FIG. 2B, the processor 314, memory 320, and/or analyzer module 330 of control unit 310 of FIG. 3, and/or the analyzer module 502 of FIGS. 5B and 5C.

The functionality of the modules of FIG. 8 may be implemented in various ways consistent with the disclosure herein. In some designs, the functionality of these modules may be implemented as one or more electrical components. In some designs, the functionality of these blocks may be implemented as a processing system including one or more processor components. In some designs, the functionality of these modules may be implemented using, for example, at least a portion of one or more integrated circuits (e.g., an ASIC). As discussed herein, an integrated circuit may include a processor, software, other related components, or some combination thereof. Thus, the functionality of different modules may be implemented, for example, as different subsets of an integrated circuit, as different subsets of a set of software modules, or a combination thereof. Also, it will be appreciated that a given subset (e.g., of an integrated circuit and/or of a set of software modules) may provide at least a portion of the functionality for more than one module.

In addition, the components and functions represented by FIG. 8, as well as other components and functions described herein, may be implemented using any suitable means. Such means also may be implemented, at least in part, using corresponding structure according to various aspects disclosed herein. For example, the components described above in conjunction with the "module for" components of FIG. 8 also may correspond to similarly designated "means for" functionality. Thus, in some aspects one or more of such means may be implemented using one or more of processor components, integrated circuits, or other suitable structure.

Figure 9:
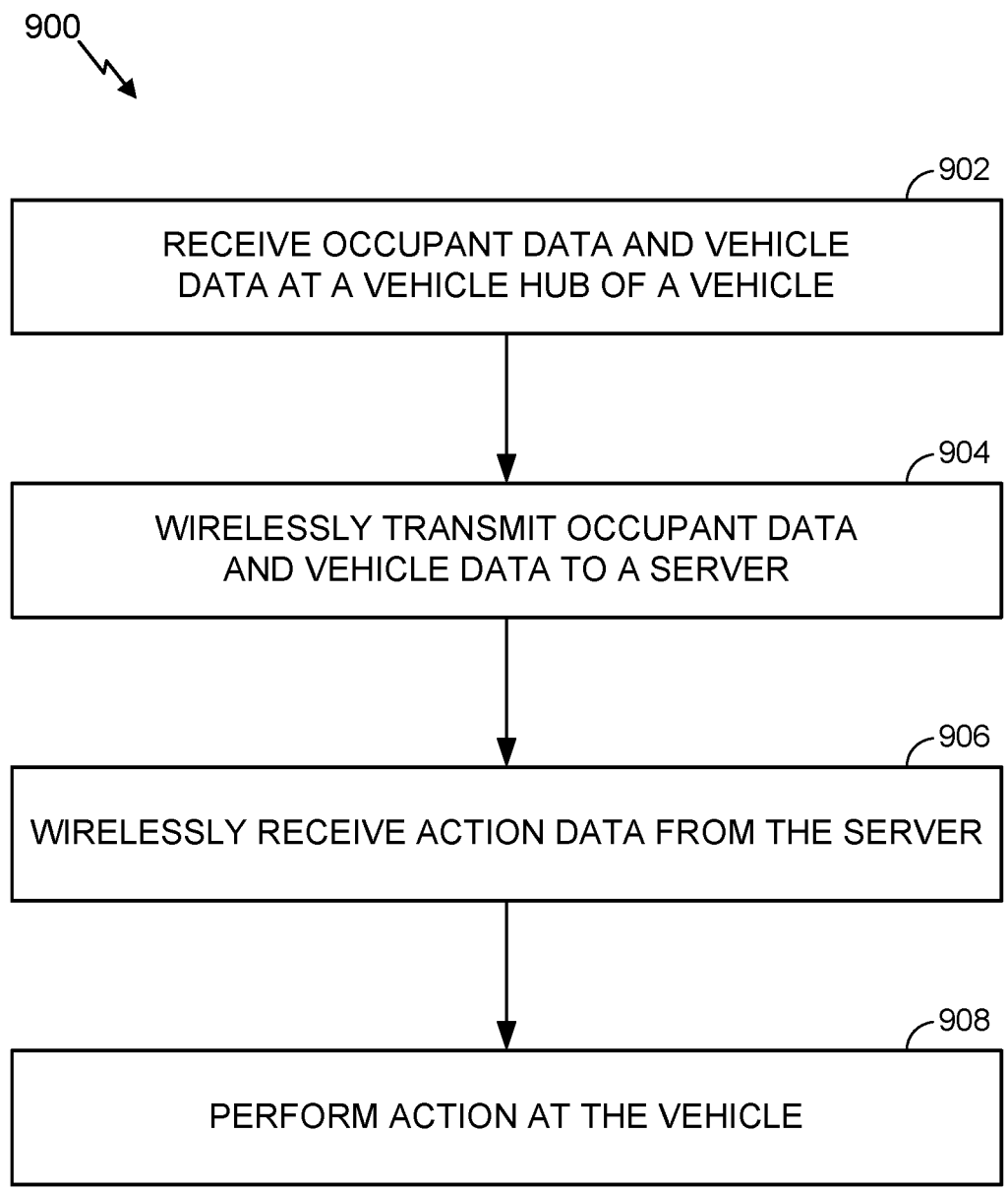
FIG. 9 is a flowchart illustrating a process, performed by a vehicle hub, of providing safe-driving support of a vehicle, according to aspects of the disclosure.

FIG. 9 is a flowchart illustrating a process 900, performed by a vehicle hub, of providing safe-driving support of a vehicle, according to aspects of the disclosure. Process 900 is an example process that may be performed by vehicle hub 220 of FIG. 2A. In process block 902, the vehicle hub 220 receives occupant data and vehicle data. For example, as discussed above with reference to FIG. 2A, vehicle hub 220 may receive occupant data and vehicle data from one or more of the illustrated domains, such as the wireless interface 202, the satellite positioning system (SPS) 204, the chassis domain 206, and the interior domain 208, the vehicle diagnostics system 210, the infotainment system 212, the powertrain domain 214, the dashboard domain 216, and one or more of the in-vehicle sensors 218. Next in process block 904, the vehicle hub 220 wirelessly transmits the occupant data and the vehicle data to a server, such as safe-driving server 170 of FIG. 1. As will be discussed below, the safe-driving server 170 may then apply the occupant data and vehicle data to a machine learning safe-driving model associated with a user profile of the occupant of the vehicle in order to generate action data.

In process block 906, the vehicle hub 220 wirelessly receives the action data from the safe-driving server 170. In process block 908, the vehicle hub may perform an action at the vehicle in response to the action data. In some aspects, performing the action based on the action data may include the automotive hub UI 256 of FIG. 2B implementing a parental control related to the occupant of the vehicle, limiting cellular data access of a mobile device located within the vehicle, disabling of text messaging by the mobile device, limiting multimedia content available by an infotainment system of the vehicle, deactivating an engine of the vehicle, limiting a speed of the vehicle, providing a route via a navigation system of the vehicle, or providing a safe-driving recommendation (e.g., alert) to a driver of the vehicle.

Figure 10:
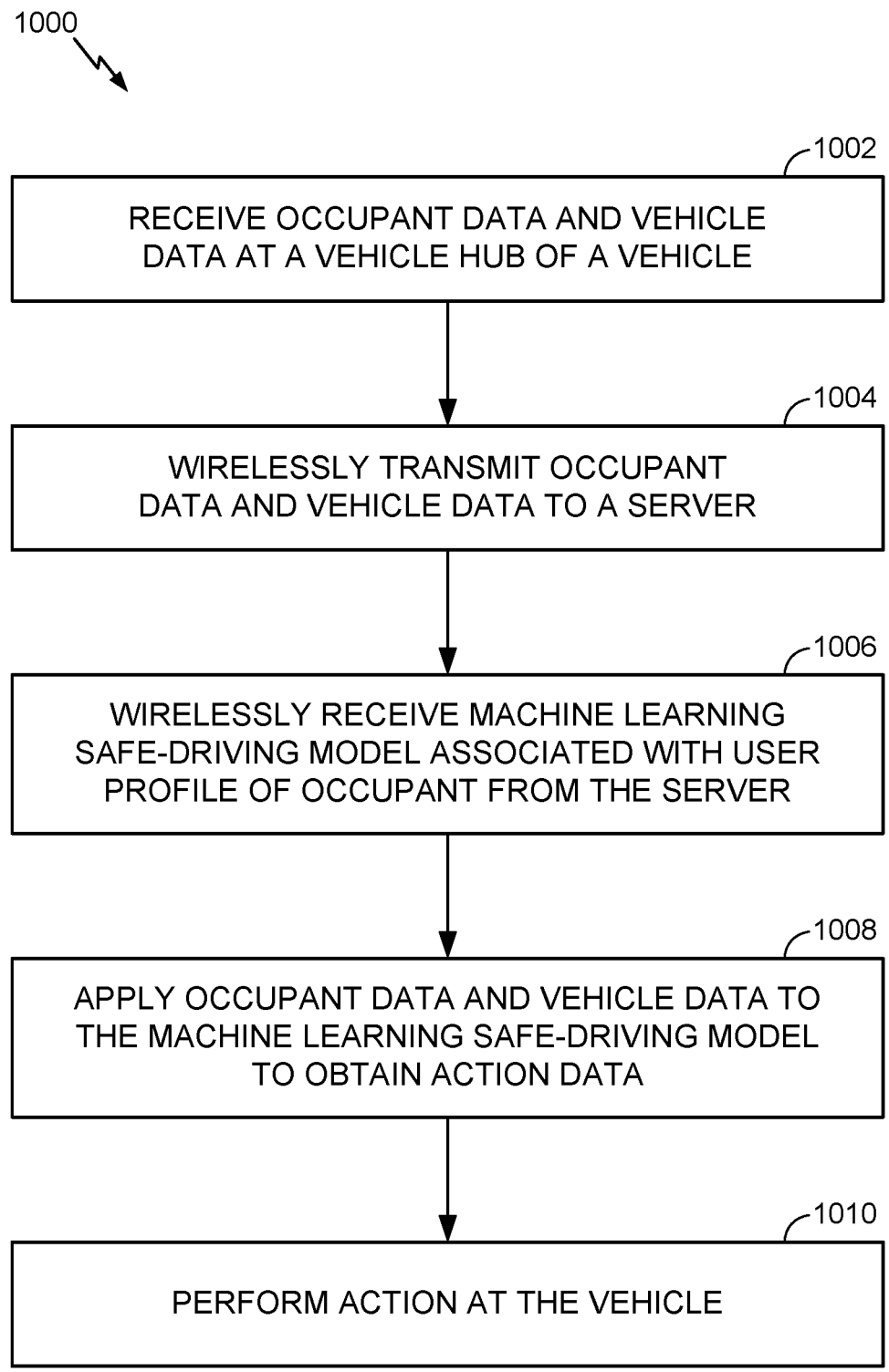
FIG. 10 is a flowchart illustrating another process, performed by a vehicle hub, of providing safe-driving support of a vehicle, according to aspects of the disclosure.

FIG. 10 is a flowchart illustrating another process 1000, performed by a vehicle hub, of providing safe-driving support of a vehicle, according to aspects of the disclosure. Process 1000 is similar to process 900 described above. However, where process 900 includes the safe-driving server 170 applying the occupant data and vehicle data to a machine learning safe-driving model, process 1000 includes the application of the occupant data and vehicle data to a machine learning safe-driving model, locally at the vehicle hub, itself. To illustrate, process block 1002 includes the vehicle hub 220 receiving the occupant data and vehicle data, where the vehicle hub 220 then wirelessly transmits the occupant data and vehicle data to the safe-driving server 170 (i.e., process block 1004). Then, in process block 1006, the vehicle hub 220 wirelessly receives a machine learning safe-driving model that is associated with a user profile of the occupant from the safe-driving server 170. In one aspect, the machine learning safe-driving model may be stored locally at the vehicle hub by way of data models module 288 of FIG. 2B. Next, in process block 1008 the analyzer module 292 of the vehicle hub 220 applies the occupant data and vehicle data to the machine learning safe-driving model stored in the data models module 288 to obtain (e.g., generate) action data. Process block 1010, then includes the vehicle hub 220 performing an action based on the action data.

Figure 11:
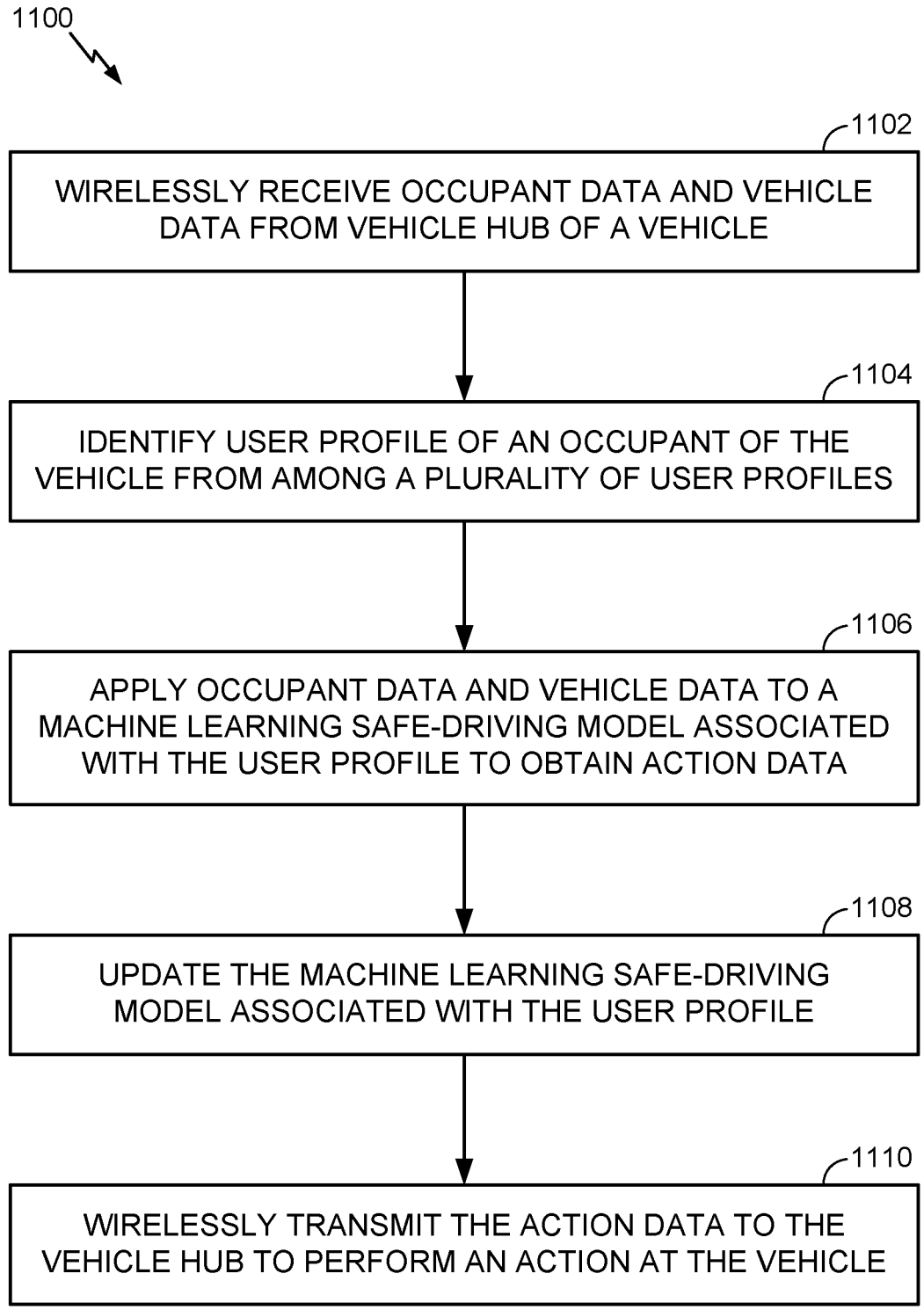
FIG. 11 is a flowchart illustrating a process, performed by a server, of providing safe-driving support of a vehicle, according to aspects of the disclosure.

FIG. 11 is a flowchart illustrating a process 1100, performed by a server, of providing safe-driving support of a vehicle, according to aspects of the disclosure. Process 1100 is one example process that may be performed by the safe-driving server 300 of FIG. 3. In process block 1102, the safe-driving server 300 wirelessly receives the occupant data and vehicle data from a vehicle hub of a vehicle. By way of example, the analyzer module 330 may receive the occupant data and vehicle data from network interface 326, where the occupant data and vehicle data was wirelessly transmitted by the vehicle (e.g., vehicle 102A of FIG. 1 may wirelessly transmit occupant data and vehicle data over air interface 104, where safe-driving server 170 receives the data either from the internet 175 or via a direct connection to core network 140).

Next, in process block 1104, the analyzer module 330 identifies a user profile of an occupant of the vehicle from among a plurality of user profiles (e.g., user profiles module 328). As mentioned above, in one aspect, analyzer module 330 may include a machine learning user identification model to identify the user profile from among the user profiles 328. In process block 1106, the analyzer module 330 may then apply the occupant data to a machine learning safe-driving model associated with the user profile identified in process block 1104. The application of the occupant data and the vehicle data to the machine learning safe-driving model may then result in the generation of one or more action data.

Process 1100 is illustrated in FIG. 11 as including an optional process block 1108 that includes updating the machine learning safe-driving model associated with the identified user profile. In one aspect, the updating of the machine learning safe-driving model may include updating the model based on the occupant data and vehicle data received in process block 1102. In other aspects, the updating of the machine learning safe-driving model may be based on other occupant data and/or vehicle data, such as past occupant data and vehicle data of the occupant of the vehicle, past occupant data and/or vehicle data of other previous occupants of the vehicle, past occupant data and/or vehicle data of the occupant that was obtained when the occupant was located in another vehicle, or occupant data and/or vehicle data of other occupants of other vehicles. According to some examples, the updating of the machine learning safe-driving model may include a supervised, unsupervised, and/or a reinforcement learning technique to improve future predictions made by the machine learning safe-driving model.

Continuing with the process 1100 of FIG. 11, process block 1110 then includes wirelessly transmitting the generated action data to the vehicle hub of the vehicle. For example, analyzer module 330 may provide the action data to network interface 326, which is then sent to the core network 140 and then wirelessly transmitted over air interface 104 to vehicle 102A.

Figure 12:
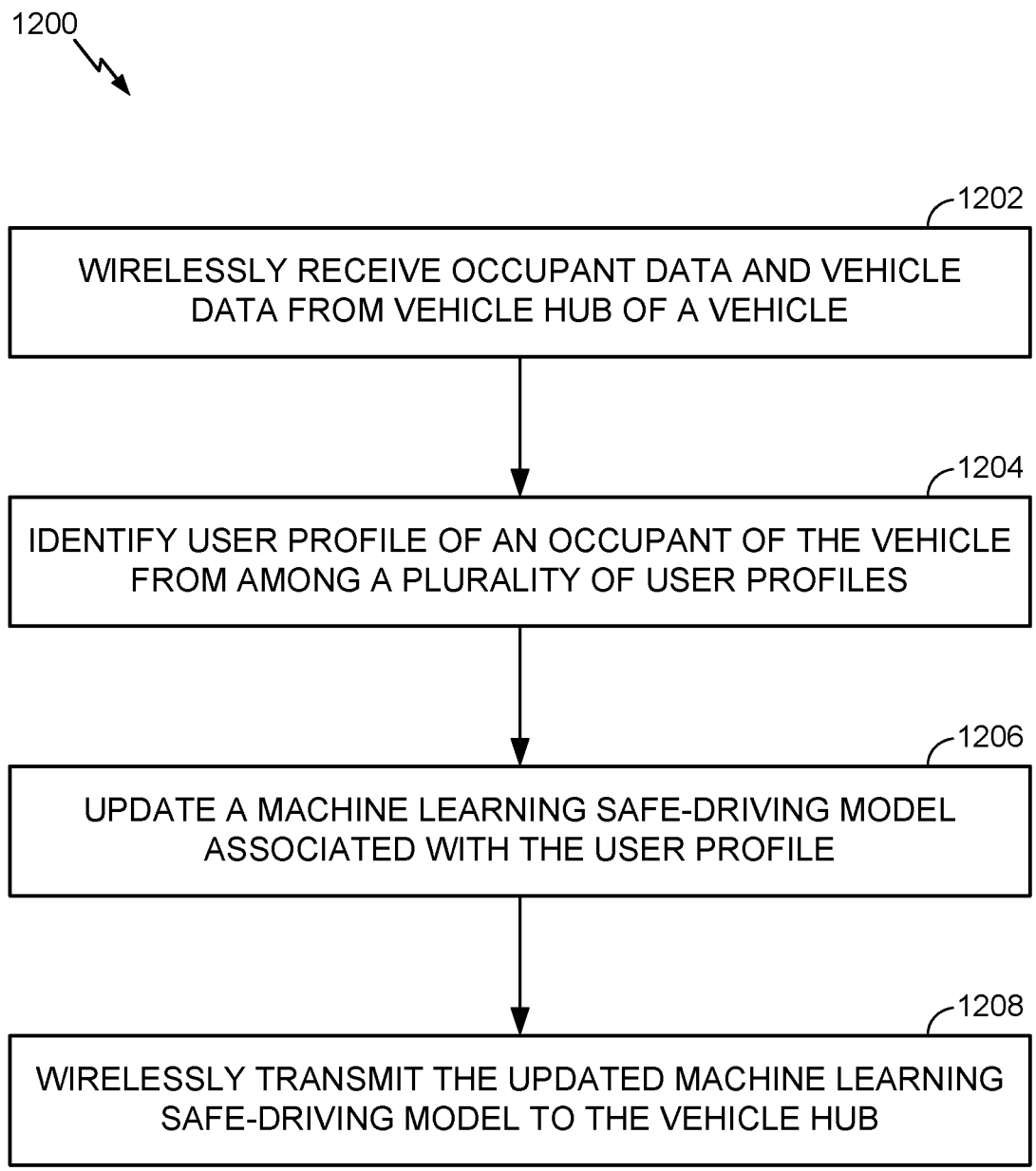
FIG. 12 is a flowchart illustrating another process, performed by a server, of providing safe-driving support of a vehicle, according to aspects of the disclosure.

FIG. 12 is a flowchart illustrating another process 1200, performed by a server, of providing safe-driving support of a vehicle, according to aspects of the disclosure. Process 1200 is similar to process 1100 described above. However, where process 1100 includes the safe-driving server 300 applying the occupant data and vehicle data to a machine learning safe-driving model at the server, process 1200 includes the safe-driving server 170 supporting the application of the occupant data and vehicle data to the machine learning safe-driving model, locally at the vehicle hub, itself. For example, in process block 1202, the safe-driving server 300 wirelessly receives the occupant data and vehicle data from a vehicle hub of a vehicle. Next, in process block 1204, the analyzer module 330 identifies a user profile of an occupant of the vehicle from among a plurality of user profiles (e.g., user profiles module 328). In process block 1206, the analyzer module 330 may then update the machine learning safe-driving model associated with the identified user profile. Next, in process block 1208 the safe driving server 300 wirelessly transmits the machine learning safe-driving model associated with the identified user profile to the vehicle hub of the vehicle.

While the foregoing disclosure shows various illustrative aspects, it should be noted that various changes and modifications may be made to the illustrated examples without departing from the scope defined by the appended claims. The present disclosure is not intended to be limited to the specifically illustrated examples alone. For example, unless otherwise noted, the functions, steps, and/or actions of the method claims in accordance with the aspects of the disclosure described herein need not be performed in any particular order. Furthermore, although certain aspects may be described or claimed in the singular, the plural is contemplated unless limitation to the singular is explicitly stated.

What is claimed is:

1. A method of providing safe-driving support of a vehicle, the method comprising:
   transmitting to a safe-driving server occupant data and vehicle data received at a vehicle hub of the vehicle, where the occupant data is related to an identity and health status of an occupant of the vehicle, and wherein the vehicle data is related to a status of the vehicle;
   receiving from the safe-driving server a machine learning safe-driving model associated with a user profile of the occupant, wherein the user profile is identified from among a plurality of user profiles based on the occupant data, and wherein the machine learning safe-driving model is one of a plurality of machine learning safe-driving models, each of the plurality of machine learning safe-driving models associated with a respective one of the plurality of user profiles maintained at the safe-driving server;
   applying the occupant data and the vehicle data to]the machine learning safe-driving model associated with the user profile of the occupant to generate action data, wherein the action data relates to an action to be performed by the vehicle while the occupant is located in the vehicle; and
   performing the action based on the action data at the vehicle, wherein performing the action at the vehicle comprises at least one of: implementing a parental control related to the occupant of the vehicle, limiting cellular data access of a mobile device located within the vehicle, disabling of text messaging by the mobile device, limiting multimedia content available by an infotainment system of the vehicle, deactivating an engine of the vehicle, limiting a speed of the vehicle, providing a route via a navigation system of the vehicle, or providing a safe-driving recommendation to a driver of the vehicle.

2. The method of claim 1, further comprising:
   receiving the occupant data at the vehicle hub of the vehicle from at least one of an in-vehicle sensor or the mobile device located within the vehicle.

3. The method of claim 2, wherein the occupant data related to the identity of the occupant comprises at least one of: an image of the occupant, a finger print of the occupant, data identifying the mobile device located within the vehicle, data indicating a position of a vehicle seat of the vehicle, data indicating a position of a steering wheel of the vehicle, or data indicating a current multimedia activity of the occupant.

4. The method of claim 2, wherein the occupant data related to the health status of the occupant comprises at least one of: data related to the health status of the occupant received at the vehicle hub from the mobile device located within the vehicle, an image of the occupant, data received at the vehicle hub from a bio-sensor located within the vehicle, data indicating a blood alcohol content of the occupant, data indicating a blood pressure of the occupant, or data indicating a heart rate of the occupant.

5. The method of claim 1, further comprising receiving the vehicle data at the vehicle hub of the vehicle from one or more of: an in-vehicle sensor, the mobile device located within the vehicle, a stationary monitor exterior to the vehicle, or another vehicle proximate to the vehicle.

6. The method of claim 5, wherein the vehicle data comprises at least one of: data indicating a current location of the vehicle, data indicating a current time, data indicating a current date, data indicating a speed of the vehicle, or data indicating a current diagnostics of one or more vehicle domains of the vehicle, wherein the one or more vehicle domains comprises at least one of: a chassis domain, a powertrain domain, a dashboard domain, or an interior domain.

7. The method of claim 1, wherein the occupant is a current driver of the vehicle.

8. The method of claim 1, wherein the occupant is a current passenger of the vehicle.

9. The method of claim 1, further comprising:
   wirelessly transmitting the occupant data and the vehicle data from the vehicle hub to the safe-driving server; and
   wirelessly receiving the machine learning safe-driving model associated with the user profile of the occupant at the vehicle hub from the safe-driving server.

10. The method of claim 1, further comprising:
    updating the machine learning safe-driving model associated with the user profile of the occupant based on the occupant data and the vehicle data received at the vehicle hub of the vehicle.

11. The method of claim 1, further comprising:
    updating the machine learning safe-driving model associated with the user profile of the occupant based on one or more of: past occupant data of the occupant of the vehicle, past occupant data of other previous occupants of the vehicle, past occupant data of the occupant obtained when the occupant was located in another vehicle, or occupant data of other occupants of other vehicles.

12. A vehicle hub for providing safe-driving support of a vehicle, the vehicle comprising:
    a processor; and
    a memory coupled to the processor, wherein the processor and memory are configured to direct the vehicle hub to:
    transmit to a safe-driving server occupant data and vehicle data received at the vehicle hub, where the occupant data is related to an identity and health status of an occupant of the vehicle, and wherein the vehicle data is related to a status of the vehicle;
    receive from the safe-driving server a machine learning safe-driving model associated with a user profile of the occupant, wherein the user profile is identified from among a plurality of user profiles based on the occupant data, and wherein the machine learning safe-driving model is one of a plurality of machine learning safe-driving models, each of the plurality of machine learning safe-driving models associated with a respective one of the plurality of user profiles maintained at the safe-driving server;
    apply the occupant data and the vehicle data to the machine learning safe-driving model associated with the user profile of the occupant to generate action data, wherein the action data relates to an action to be performed by the vehicle while the occupant is located in the vehicle; and
    perform the action at the vehicle in response to the action data, wherein performing the action at the vehicle comprises at least one of: implementing a parental control related to the occupant of the vehicle, limiting cellular data access of a mobile device located within the vehicle, disabling of text messaging by the mobile device, limiting multimedia content available by an infotainment system of the vehicle, deactivating an engine of the vehicle, limiting a speed of the vehicle, providing a route via a navigation system of the vehicle, or providing a safe-driving recommendation to a driver of the vehicle.

13. The vehicle hub of claim 12, wherein the vehicle hub is configured to receive occupant data from at least one of an in-vehicle sensor or the mobile device located within the vehicle.

14. The vehicle hub of claim 12, wherein the processor and memory are further configured to direct the vehicle hub to:
wirelessly transmit the occupant data and the vehicle data from the vehicle hub to the safe-driving server; and
wirelessly receive the machine learning safe-driving model associated with the user profile of the occupant at the vehicle hub from the safe-driving server.

15. A server for providing safe-driving support of a vehicle, the server comprising:
a processor; and
a memory coupled to the processor, wherein the processor and memory are configured to direct the server to:
receive occupant data and vehicle data received at a vehicle hub of the vehicle, where the occupant data is related to an identity and health status of an occupant of the vehicle, and wherein the vehicle data is related to a status of the vehicle;
identify a user profile of the occupant from among a plurality of user profiles based on the occupant data;
apply the occupant data and the vehicle data to a machine learning safe-driving model to generate action data, wherein the machine learning safe-driving model is associated with the user profile of the occupant, wherein the machine learning safe-driving model is one of a plurality of machine learning safe-driving models, each of the plurality of machine learning safe-driving models associated with a respective one of the plurality of user profiles maintained at the server, and wherein the action data relates to an action to be performed by the vehicle while the occupant is located in the vehicle; and
wirelessly transmit the action data to the vehicle hub to perform the action at the vehicle, wherein performing the action at the vehicle comprises at least one of: implementing a parental control related to the occupant of the vehicle, limiting cellular data access of a mobile device located within the vehicle, disabling of text messaging by the mobile device, limiting multimedia content available by an infotainment system of the vehicle, deactivating an engine of the vehicle, limiting a speed of the vehicle, providing a route via a navigation system of the vehicle, or providing a safe-driving recommendation to a driver of the vehicle.

16. The server of claim 15, wherein the processor and memory are further configured to direct the server to:
update the machine learning safe-driving model associated with the user profile of the occupant based on the occupant data and the vehicle data.

17. The server of claim 15, wherein the processor and memory are further configured to direct the server to:
update the machine learning safe-driving model associated with the user profile of the occupant based on one or more of: past occupant data of the occupant of the vehicle, past occupant data of other previous occupants of the vehicle, past occupant data of the occupant obtained when the occupant was located in another vehicle, or occupant data of other occupants of other vehicles.

18. The server of claim 15, wherein the processor and memory are further configured to direct the server to:
wirelessly transmit an updated machine learning safe-driving model associated with the user profile of the occupant to the vehicle hub.

19. An apparatus for providing safe-driving support of a vehicle, the apparatus comprising:
means for transmitting to a safe-driving server occupant data and vehicle data received at a vehicle hub of the vehicle, where the occupant data is related to an identity and health status of an occupant of the vehicle, and wherein the vehicle data is related to a status of the vehicle;
means for receiving from the safe-driving server a machine learning safe-driving model associated with a user profile of the occupant, wherein the user profile is identified from among a plurality of user profiles based on the occupant data, and wherein the machine learning safe-driving model is one of a plurality of machine learning safe-driving models, each of the plurality of machine learning safe-driving models associated with a respective one of the plurality of user profiles maintained at the safe-driving server;
means for applying of the occupant data and the vehicle data to the machine learning safe-driving model associated with the user profile of the occupant to generate action data, wherein the action data relates to an action to be performed by the vehicle while the occupant is located in the vehicle; and
means for performing the action based on the action data at the vehicle, wherein performing the action at the vehicle comprises at least one of: implementing a parental control related to the occupant of the vehicle, limiting cellular data access of a mobile device located within the vehicle, disabling of text messaging by the mobile device, limiting multimedia content available by an infotainment system of the vehicle, deactivating an engine of the vehicle, limiting a speed of the vehicle, providing a route via a navigation system of the vehicle, or providing a safe-driving recommendation to a driver of the vehicle.

20. The apparatus of claim 19, further comprising:
means for updating the machine learning safe-driving model associated with the user profile of the occupant based on the occupant data and the vehicle data received at the vehicle hub of the vehicle.

21. The apparatus of claim 19, further comprising:
means for updating the machine learning safe-driving model associated with the user profile of the occupant based on one or more of: past occupant data of the occupant of the vehicle, past occupant data of other previous occupants of the vehicle, past occupant data of the occupant obtained when the occupant was located in another vehicle, or past occupant data of other occupants of other vehicles.

22. A non-transitory computer-readable storage medium including program code stored thereon for providing safe-driving support of a vehicle, the program code comprising instructions to:
transmit to a safe-driving server occupant data and vehicle data received at a vehicle hub of the vehicle, where the occupant data is related to an identity and health status of an occupant of the vehicle, and wherein the vehicle data is related to a status of the vehicle;
receive from the safe-driving server a machine learning safe-driving model associated with a user profile of the occupant, wherein the user profile is identified from among a plurality of user profiles based on the occupant data, and wherein the machine learning safe-driving model is one of a plurality of machine learning safe-driving models, each of the plurality of machine learning safe-driving models associated with a respective one of the plurality of user profiles maintained at the safe-driving server;

apply the occupant data and the vehicle data to the machine learning safe-driving model associated with the user profile of the occupant to generate action data, wherein the action data relates to an action to be performed by the vehicle while the occupant is located in the vehicle; and perform the action based on the action data at the vehicle, wherein performing the action at the vehicle comprises at least one of: implementing a parental control related to the occupant of the vehicle, limiting cellular data access of a mobile device located within the vehicle, disabling of text messaging by the mobile device, limiting multimedia content available by an infotainment system of the vehicle, deactivating an engine of the vehicle, limiting a speed of the vehicle, providing a route via a navigation system of the vehicle, or providing a safe-driving recommendation to a driver of the vehicle.

23. The non-transitory computer-readable storage medium of claim 22, wherein the program code further comprises instructions to:
update the machine learning safe-driving model associated with the user profile of the occupant based on the occupant data and the vehicle data received at the vehicle hub of the vehicle.

24. The non-transitory computer-readable storage medium of claim 22, wherein the program code further comprises instructions to:
update the machine learning safe-driving model associated with the user profile of the occupant based on one or more of: past occupant data of the occupant of the vehicle, past occupant data of other previous occupants of the vehicle, past occupant data of the occupant obtained when the occupant was located in another vehicle, or occupant data of other occupants of other vehicles.

* * * * *